(12) United States Patent
De Gelder et al.

(10) Patent No.: US 12,201,097 B2
(45) Date of Patent: Jan. 21, 2025

(54) CLIMATE SYSTEM AND METHOD FOR REARING INVERTEBRATES

(71) Applicant: Protix B.V., Dongen (NL)

(72) Inventors: Vincent De Gelder, Gorinchem (NL);
Maurits Petrus Maria Jansen, Bavel (NL); Kees Wilhelmus Petrus Aarts, Vught (NL); Stefan Bazelmans, Steensel (NL); Eric Holland Schmitt, Antwerp (BE)

(73) Assignee: Protix B.V., Dongen (NL)

( * ) Notice: Subject to any disclaimer, the term of this patent is extended or adjusted under 35 U.S.C. 154(b) by 78 days.

(21) Appl. No.: 18/255,373

(22) PCT Filed: Dec. 2, 2021

(86) PCT No.: PCT/NL2021/050730
§ 371 (c)(1),
(2) Date: Jun. 1, 2023

(87) PCT Pub. No.: WO2022/119443
PCT Pub. Date: Jun. 9, 2022

(65) Prior Publication Data
US 2024/0032517 A1 Feb. 1, 2024

(30) Foreign Application Priority Data
Dec. 3, 2020 (NL) .................................. 2027034

(51) Int. Cl.
*A01K 67/00* (2006.01)
*A01K 67/033* (2006.01)

(52) U.S. Cl.
CPC ................. *A01K 67/033* (2013.01)

(58) Field of Classification Search
USPC ............................................. 119/6.5
See application file for complete search history.

(56) References Cited

U.S. PATENT DOCUMENTS

| | | | | |
|---|---|---|---|---|
| 5,036,797 | A * | 8/1991 | Koozer | A01K 1/0058 119/448 |
| 8,602,837 | B1 * | 12/2013 | Allan | A01K 47/00 449/27 |
| 11,382,317 | B2 * | 7/2022 | Jansen | A01K 67/033 |
| 11,684,045 | B2 * | 6/2023 | Drennan | A01K 1/0047 449/6 |
| 11,882,817 | B2 * | 1/2024 | De Gelder | A01K 67/033 |
| 2011/0146582 | A1 * | 6/2011 | Lemmon | F24F 11/56 454/258 |
| 2020/0146270 | A1 * | 5/2020 | Calis | A01K 67/033 |
| 2021/0007304 | A1 * | 1/2021 | Kuhns | A01G 7/045 |
| 2022/0061232 | A1 * | 3/2022 | Whelan | B65G 1/065 |
| 2022/0304290 | A1 | 9/2022 | De Gelder et al. | |

FOREIGN PATENT DOCUMENTS

| | | | |
|---|---|---|---|
| WO | 2014171829 A1 | 10/2014 | |
| WO | 2019022596 A1 | 1/2019 | |
| WO | 2020/246878 A1 | 12/2020 | |

* cited by examiner

*Primary Examiner* — Yvonne R Abbott-Lewis
(74) *Attorney, Agent, or Firm* — N.V. Nederlandsch Octrooibureau

(57) ABSTRACT

Systems and methods are provided for rearing invertebrates by utilizing a plurality of crates arranged into at least one stack, each crate in the stack defining an airflow path there through from an inlet opening in a first wall to an outlet opening in a second wall opposite the first wall of each crate. The plurality of crates are arranged in a climate controlled chamber.

20 Claims, 11 Drawing Sheets

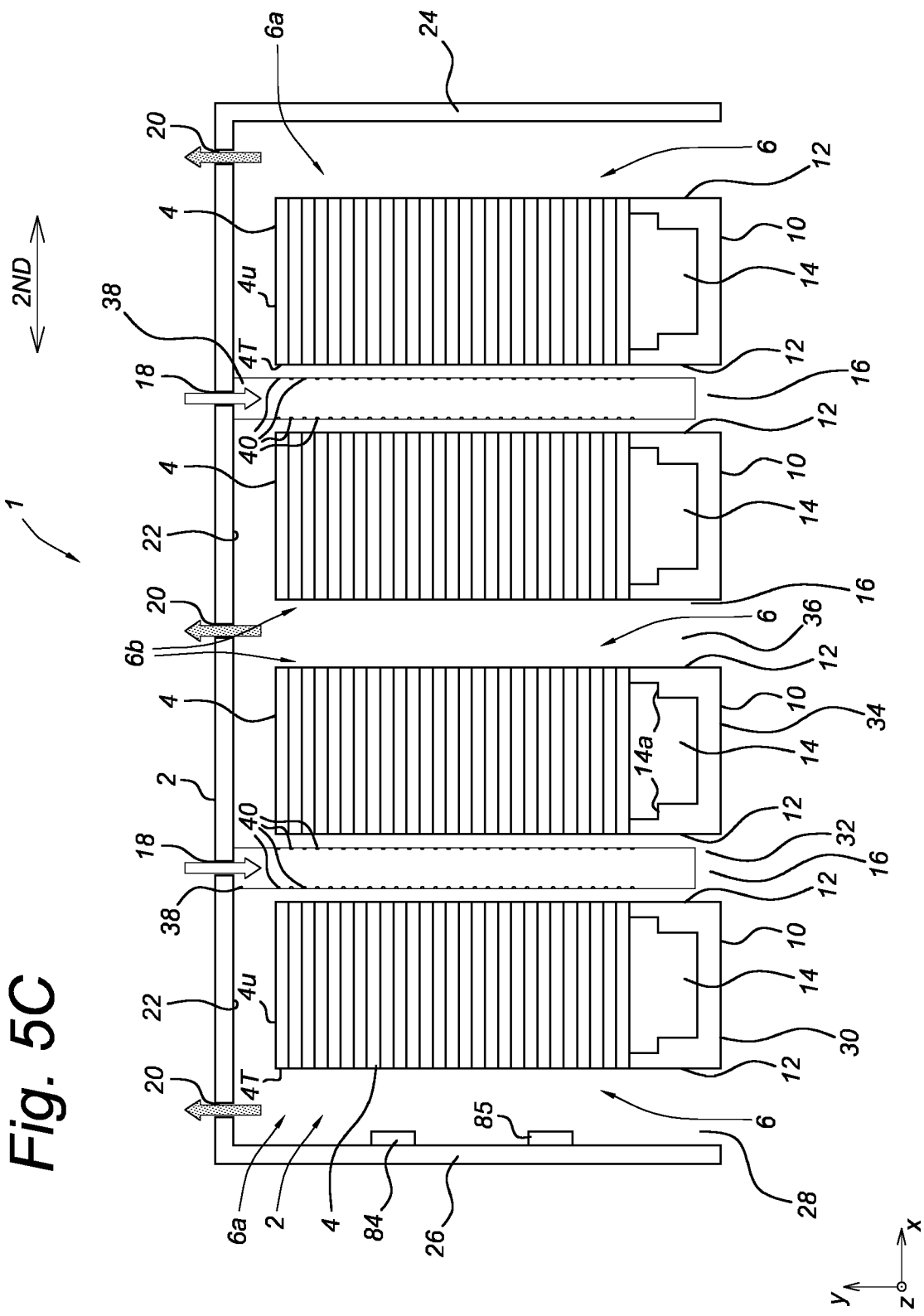

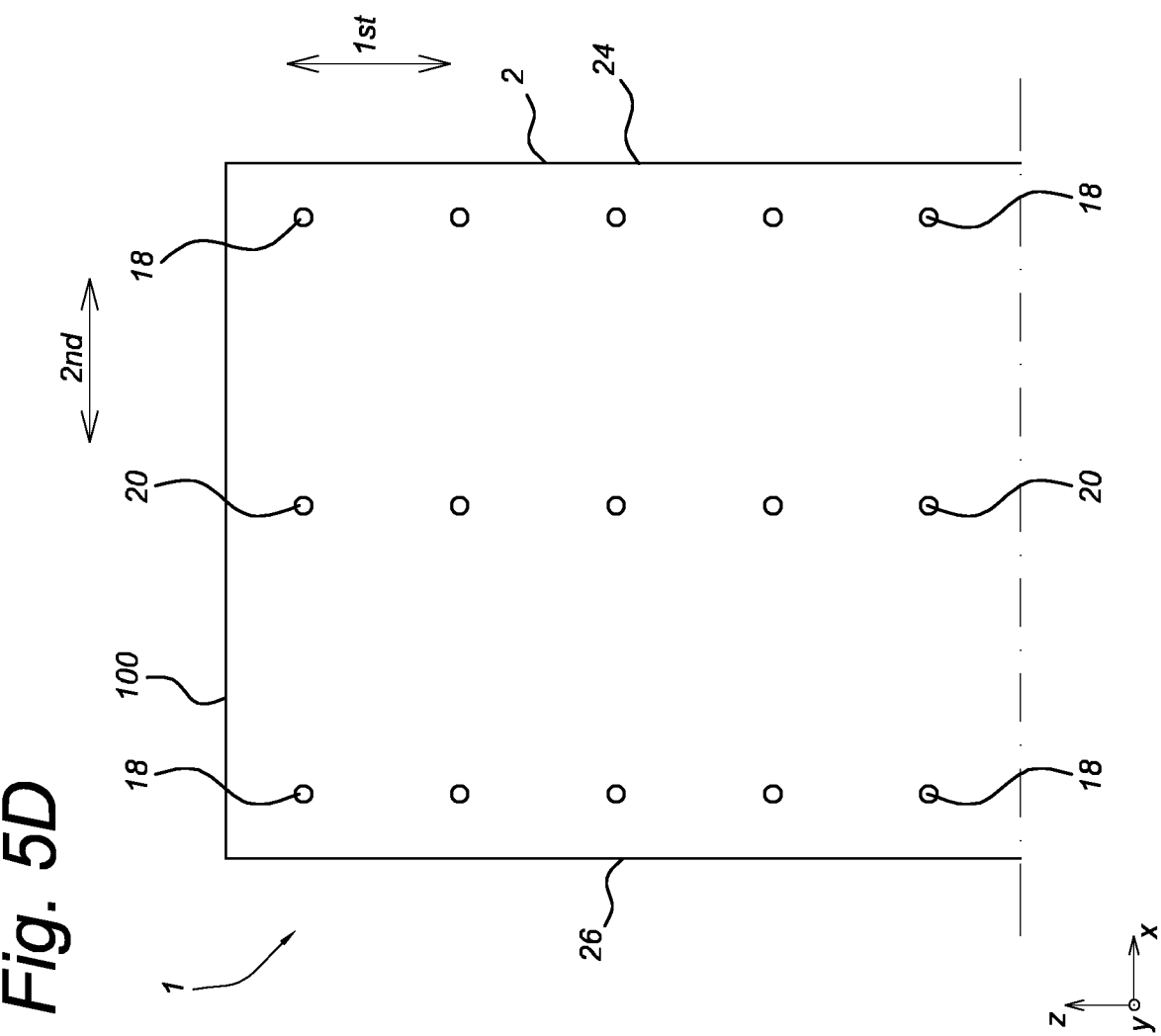

CLIMATE SYSTEM AND METHOD FOR REARING INVERTEBRATES

TECHNICAL FIELD

The invention relates to a method and system for rearing invertebrates, more specifically insects, in a climate controlled environment.

BACKGROUND TO THE INVENTION

Insects and their larvae can be used as an animal protein feeds, and for this purpose it may be desirable to farm insects on a large scale. Systems for producing and/or breeding insects on a large scale are known in the art.

For example, U.S. Pat. No. 5,158,497 discloses an illuminated dome for the controlled mixing of flying insects. International Patent Publication No. WO 2014/171829 describes a method and system for breeding insects in a climate controlled environment. The system and method comprises a plurality of stacked crates configured to contain insects and/or larvae, and a system for controlling airflow through the crates.

Problems associated with known systems may include inadequate or inconsistent climate control, insect containment issues, limited capacity for observation, and disruptive insect or larvae 'crawl out' (where larvae and/or insects escape from a designated area).

SUMMARY OF THE INVENTION

The present invention seeks to solve one or more of the above problems by providing an improved system and method for insect rearing.

Accordingly, in a first aspect of the invention, there is provided a system for rearing invertebrates, the system comprises
  a plurality of crates arranged into at least one stack, each crate in the stack defining an airflow path there through from an inlet opening in a first wall to an outlet opening in a second wall opposite the first wall;
  a climate chamber comprising:
    an internal volume enclosed by walls, a floor, and a ceiling;
    a first row of air outlets extending in a first direction 1ST within the internal volume;
    a first row of air inlets located next to the first row of air outlets, and extending parallel thereto, and spaced apart from the first row of air outlets in a second direction 2ND, perpendicular to the first direction 1ST;
    at least one first stack of crates arranged in a space between the first row of air outlets and the first row of air inlets;
    a conduit extending from each of the plurality of air inlets along the first stack of crates, said conduit comprising a plurality of conduit openings configured to align with inlet openings of the plurality of crates in the stack;
    wherein the crates are arranged with the airflow path oriented perpendicular to the first direction 1ST.
An embodiment is the system for rearing invertebrates of the invention, the system comprising:
  a plurality of crates arranged into at least one stack, each crate in the stack defining an airflow path there through from an inlet opening in a first wall to an outlet opening in a second wall opposite the first wall;
  a climate chamber comprising:
    an internal volume enclosed by walls, a floor, and a ceiling;
    a first row of air outlets extending in a first direction 1ST within the internal volume; a second row of air outlets extending parallel to the first row of air outlets within the internal volume;
    a row of air inlets located between the first and second rows of air outlets, and extending parallel thereto, and spaced apart from the first and second rows of air outlets in a second direction 2ND, perpendicular to the first direction 1ST;
    at least one first stack of crates arranged in a space between the first row of air outlets and the row of air inlets;
    at least one second stack of crates arranged in a space between the second row of air outlets and the row of air inlets;
    a conduit extending from each of the plurality of air inlets between the first and second stack of crates, said conduit comprising a plurality of conduit openings configured to align with inlet openings of the plurality of crates in each stack;
  or
    an internal volume enclosed by walls, a floor, and a ceiling;
    a first row of air inlets extending in a first direction 1ST within the internal volume; a second row of air inlets extending parallel to the first row of air inlets within the internal volume;
    a first row of air outlets located between the first and second rows of air inlets, and extending parallel thereto, and spaced apart from the first and second rows of air inlets in a second direction 2ND, perpendicular to the first direction 1ST;
    at least one first stack of crates arranged in a space between the first row of air inlets and the first row of air outlets;
    at least one second stack of crates arranged in a space between the second row of air inlets and the first row of air outlets;
    a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack;
    wherein the crates are arranged with the airflow path oriented perpendicular to the first direction 1ST.

The system of the present invention allows for a tightly controlled, automated environment for growing insects, e.g. such as living insect larvae, e.g. black soldier fly (BSF) larvae. In particular, the system provides accurate control of environmental conditions in each crate, thereby ensuring an even, consistent, and predictable growth of insects within each crate and thus consistent and predictable growth of insects in each stack of crates. An embodiment is the system for rearing invertebrates of the invention, wherein the plurality of crates are arranged into one to eight stacks, preferably any one of one, two, three, four, five, six stacks, more preferably any one of one, two or three stacks, most preferably one stack or two stacks, wherein the two or more stacks, when present, extend in the second direction 2ND perpendicular to the first direction 1ST with the climate chamber in the direction of the airflow path oriented perpendicular to the first direction 1ST.

In a second aspect of the invention, there is provided a method for rearing invertebrates, the method comprising the steps of:
(i) providing a plurality of crates, each crate having a first opening in a first wall and a second opening in a second wall opposite the first opening to define a first air flow path between the first and second openings;
(ii) filling at least a portion of each crate of the plurality of crates with a substrate and a plurality of invertebrates at a first developmental stage;
(iii) stacking the plurality of crates;
(iii) providing a climate chamber comprising:
an internal volume enclosed by walls, a floor, and a ceiling;
a first row of air outlets extending in a first direction 1ST within the internal volume;
a first row of air inlets located next to the first row of air outlets, and extending parallel thereto, and spaced apart from the first row of air outlets in a second direction 2ND, perpendicular to the first direction 1ST;
at least one first stack of crates arranged in a space between the first row of air outlets and the first row of air inlets;
a conduit extending from each of the plurality of air inlets along the first stack of crates, said conduit comprising a plurality of conduit openings configured to align with inlet openings of the plurality of crates in the stack;
(iv) positioning at least one stack of crates wherein the crates are arranged with the airflow path oriented perpendicular to the first direction 1ST and in the second direction 2ND;
(v) applying a pressure differential between the air inlet and the air outlet.

An embodiment is the method of the invention, wherein in step (iii) the climate chamber comprises:
an internal volume enclosed by walls, a floor, and a ceiling;
a first row of air outlets extending in a first direction 1ST within the internal volume; a second row of air outlets extending parallel to the first row of air outlets within the internal volume;
a row of air inlets located between the first and second rows of air outlets, and extending parallel thereto, and spaced apart from the first and second rows of air outlets in a second direction 2ND, perpendicular to the first direction 1ST;
at least one first stack of crates arranged in a space between the first row of air outlets and the row of air inlets;
at least one second stack of crates arranged in a space between the second row of air outlets and the row of air inlets;
a conduit extending from each of the plurality of air inlets between the first and second stack of crates, said conduit comprising a plurality of conduit openings configured to align with inlet openings of the plurality of crates in each stack;
or
wherein in step (iii) the climate chamber comprises:
an internal volume enclosed by walls, a floor, and a ceiling;

a first row of air inlets extending in a first direction 1ST within the internal volume; a second row of air inlets extending parallel to the first row of air inlets within the internal volume;
a first row of air outlets located between the first and second rows of air inlets, and extending parallel thereto, and spaced apart from the first and second rows of air inlets in a second direction 2ND, perpendicular to the first direction 1ST;
at least one first stack of crates arranged in a space between the first row of air inlets and the first row of air outlets;
at least one second stack of crates arranged in a space between the second row of air inlets and the first row of air outlets;
a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack.

The method of the present invention provides the same advantages as the aforementioned system, i.e. allowing for tight control and automation of growing insects, e.g. such as living insect larvae, for example BSF larvae, such as BSF larvae 0-5 days of age or BSF larvae 4-20 days of age, e.g. 5-16 days of age. The method provides accurate control of environmental conditions in each crate, thereby ensuring even, consistent and predictable growth of insects within each crate and thus consistent and predictable growth of insects in each stack of crates.

So given the system and method of the present invention, problems often encountered in the prior art may be dealt with and resolved in that adequate and consistent climate control is provided, containment issues are eliminated or significantly reduced, sufficient or improved capacity for observation is achieved, and insect/larvae 'crawl out' is prevented or mitigated.

In a third aspect of the invention, there is provided an invertebrate rearing crate configured for use in the aforementioned system and/or in the aforementioned method, wherein the crate comprises a base, upstanding side walls and upstanding end walls defining a perimeter around the base, and at least one sensor mounting region in the base of the crate.

The invertebrate rearing crate of the present invention allows for more accurate monitoring of environmental conditions in a crate and as such the crate is ideally suited for use in the system and/or method above for achieving adequate and consistent climate control. Moreover, the crate is ideally suited for use in the system and/or the method above for prevention of insect/larvae 'crawl out' and for prevention of contamination of the system by larvae crawled out of the crate.

BRIEF DESCRIPTION OF THE FIGURES

The present invention will now be described with reference to a number of non-limiting, illustrative examples, as shown in the following drawings, in which:

FIG. 5C shows a climate chamber in accordance with an embodiment of the invention, the climate chamber containing a plurality of crates;

FIG. 5D shows a top view of a climate chamber in accordance with an embodiment of the invention, the climate chamber containing a plurality of air inlets 18 and air outlets 20;

DETAILED DESCRIPTION OF THE DRAWINGS

Figure 1A:
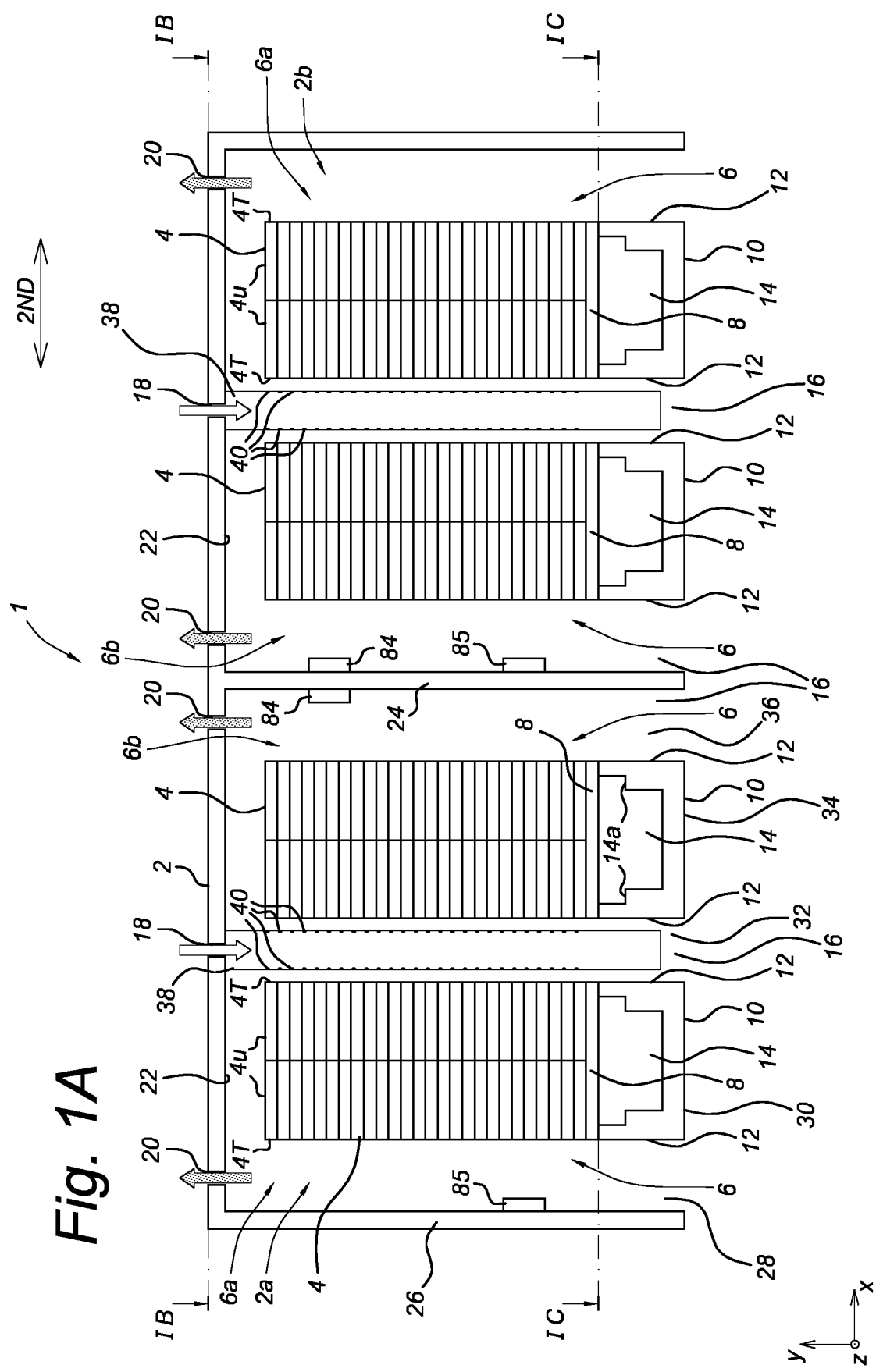
FIG. 1A shows a climate chamber in accordance with an embodiment of the invention, the climate chamber containing a plurality of crates.
Figure 1B:
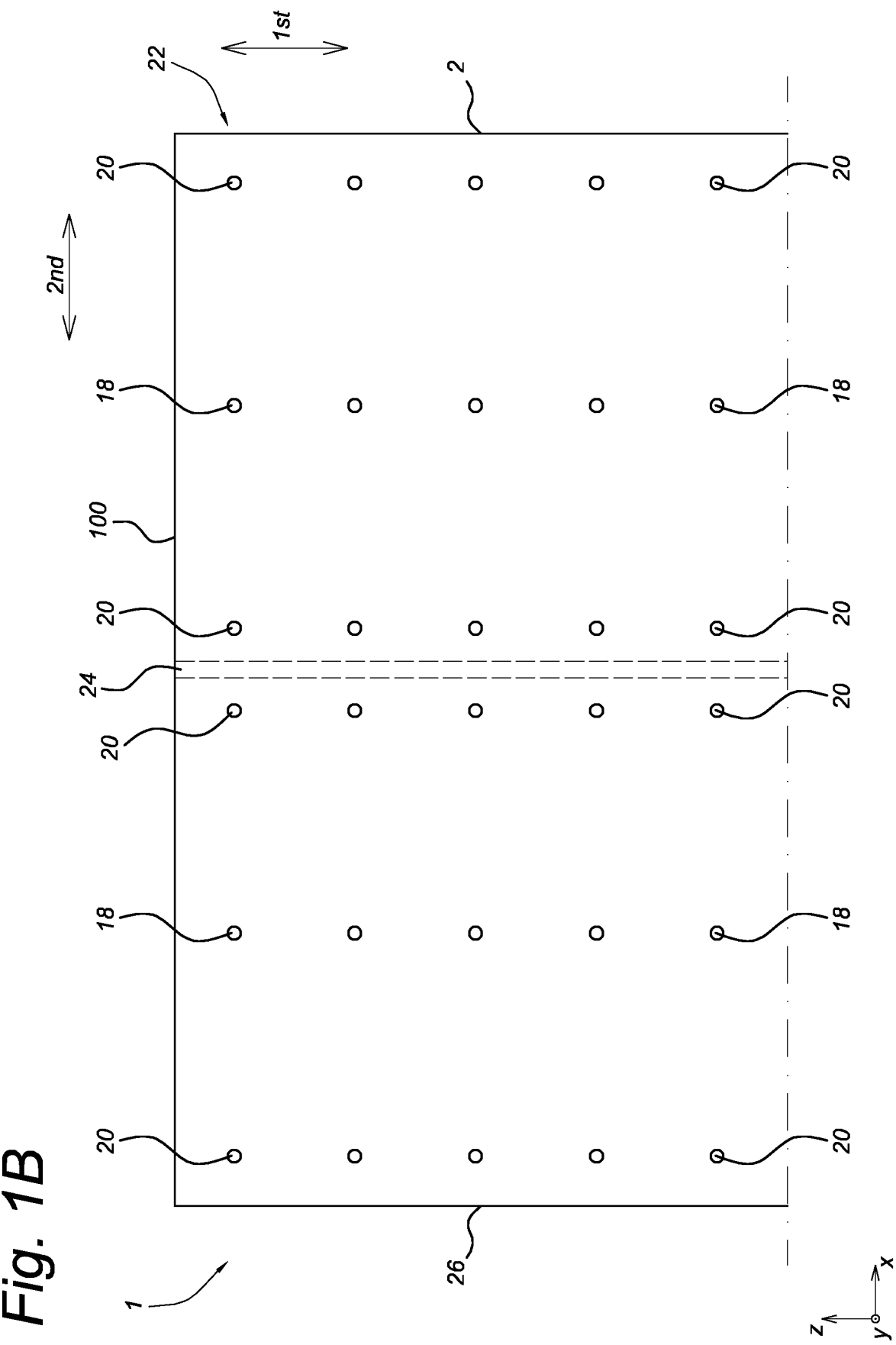
FIG. 1B shows a top view of the climate chamber shown in FIG. 1A in accordance with an embodiment of the invention, the climate chamber containing a plurality of air inlets 18 and air outlets 20.

An exemplary system 1 according to the invention is shown in FIG. 1A and FIG. 1B, which shows a front view of a climate chamber 2 configured to contain a plurality of crates 4 and which shows a top view of said climate chamber 2. The crates 4 are arranged in stacks 6. In the illustrated embodiment, each stack of crates rests on a pallet 8. Each pallet 8 receives four stacks of crates 4, in a 2×2 arrangement. However, it will be appreciated that a pallet 8 can comprise more than four stacks of crates or fewer than four stacks of crates. Moreover, in some embodiments, the system does not comprise pallets for receiving stacks of crates. In such embodiments, the stacks of crates rest on a track 10 that comprises a pair of upstanding walls 12 separated from each other by a channel 14. The upstanding walls 12 are configured to support the stacks of crates above the channel 14. The track 10 is configured to receive one or multiple stacks of crates, e.g. by arranging the stacks of crates in rows, i.e. rows of stacks of crates in the first direction.

Each pallet 8 rests on a track 10 that comprises a pair of upstanding walls 12 separated from each other by a channel 14. The upstanding walls 12 are configured to support the pallets 8 above the channel 14. The track 10 is configured to receive one or multiple pallets 8, e.g. by arranging the pallets 8 in rows. An embodiment is the system of the invention, wherein the climate chamber 1 further comprises at least one track 10 extending in the first direction 1ST with the climate chamber, said track comprising a first wall 12 and a second wall 12, and a channel 14 defined there between. An embodiment is the system 1 of the invention, wherein the plurality of crates 4 are arranged into one to eight stacks 6, 6a, 6b, preferably any one of one, two, three, four, five, six stacks 6, more preferably any one of one, two or three stacks, most preferably one stack or two stacks, wherein the two or more stacks, when present, extend in the second direction 2ND perpendicular to the first direction 1ST with the climate chamber 1 in the direction of the airflow path oriented 80a perpendicular to the first direction 1ST. When two or more of such stacks 6 of crates 4 are positioned side by side in the second direction 2ND, such stack of crates are supported by the pallet 8 which in turn is supported by the upstanding walls 12 of a track 10 receiving the pellet comprising the stacks of crates.

An embodiment is the system of the invention, wherein the climate chamber further comprises at least one track 10 extending in the first direction 1ST with the climate chamber 1, said track comprising a first wall 12 and a second wall 12, and a channel 14 defined there between, wherein the track is positioned between the first row of air outlets 20 and the first row of air inlets 18, and wherein the system preferably comprises a second track 10 positioned between the first row of air inlets 18 and the second row of air outlets 20 or comprises a second track 10 positioned between the first row of air outlets 20 and the second row of air inlets 18.

An embodiment is the system of the invention, wherein the at least one track 10 comprises a pair of walls 12 separated from each other by a channel 14, said channel extending in the second direction 2ND, which is perpendicular to the first direction 1ST; and optionally, wherein the at least one stack 6 of crates 4 is arranged on the tracks 10 such that the airflow path 80a extends in the first direction 1ST.

An embodiment is the system 1 of the invention, wherein each track 10 is configured to support a row of crate stacks 6 above the channel 14, the row of stacks extending in the first direction 1ST with the climate chamber 1.

An embodiment is the system 1 of the invention, wherein each track 10 is configured to support a pallet 8, the pallet comprising at least one stack 6, 6a, 6b of crates 4, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement.

An embodiment is the system 1 of the invention, wherein each of the walls 12 of the track 10 is a solid wall 12 and separates the channel 14 from an adjacent gutter 16.

Each track 10 is separated from an adjacent track 10 by a gutter 16. Each gutter 16 is separated from an adjacent channel 14 by an upstanding wall 12 that forms one of a pair of upstanding walls 12. In this manner, a series of parallel tracks 10 can be formed, each separated from each other by the gutter 16, with a channel 14 formed under each row of pallets 8 or formed under each row of stacks 6 of crates 4.

It will be appreciated that the system 1 can be configured such that the pallets 8 are omitted, and the stacks of crates 4 rest directly on the tracks 10, e.g. on the upstanding walls 12 of the tracks 10. However, in such an embodiment the dimension of the crates 4 should be sufficient to span the width of the channel 14, to rest on the upstanding walls 12 that form the track 10. Alternatively, the crates 4 can be secured to each other along adjacent edges 44 and/or 46 (see e.g. FIG. 3A) to span the channel 10 and support the stack of crates 6 above.

As shown in FIG. 1, the climate chamber 2 comprises a generally closed volume. Access to the chamber 2 is possible through openings, for example, windows, doors, access shafts. However, the chamber 2 is preferably a substantially closed volume when all access points (e.g. doors, windows, hatches) are closed. The chamber 2 can be an internal space in a fixed building, or it can be an internal volume of a portable structure, for example, a shipping container, a reefer, a truck trailer, a freight plane.

Each chamber 2 can comprise a plurality of multiple rows of stacked crates 4. The climate chamber 2 is configured with a ventilation or climate control system 84 configured to manage and control the climate conditions within the crates 4. To ensure that the larvae and/or insects stored within the crates develop at the same or similar rates, the climate conditions within the crates 4 (e.g. temperature, humidity) are closely controlled.

The climate control system 1 preferably comprises at least one air inlet 18 configured to introduce climate controlled air to the chamber 2, and at least one air outlet 20, or exhaust opening 20, configured to extract or draw air from the chamber 2.

The air inlet(s) 18 are preferably provided on a first side of the crates and the air outlet(s) 20 are preferably provided on a second side of the crates 4. By providing (an) air inlet(s) 18 on a first side of a stack of crates 4, and an air outlet 20 on an opposing side of the stack of crates 4, a flow of climate controlled air 80 along air flow paths 80a through or across the crates 4 can be achieved.

Figure 3A:
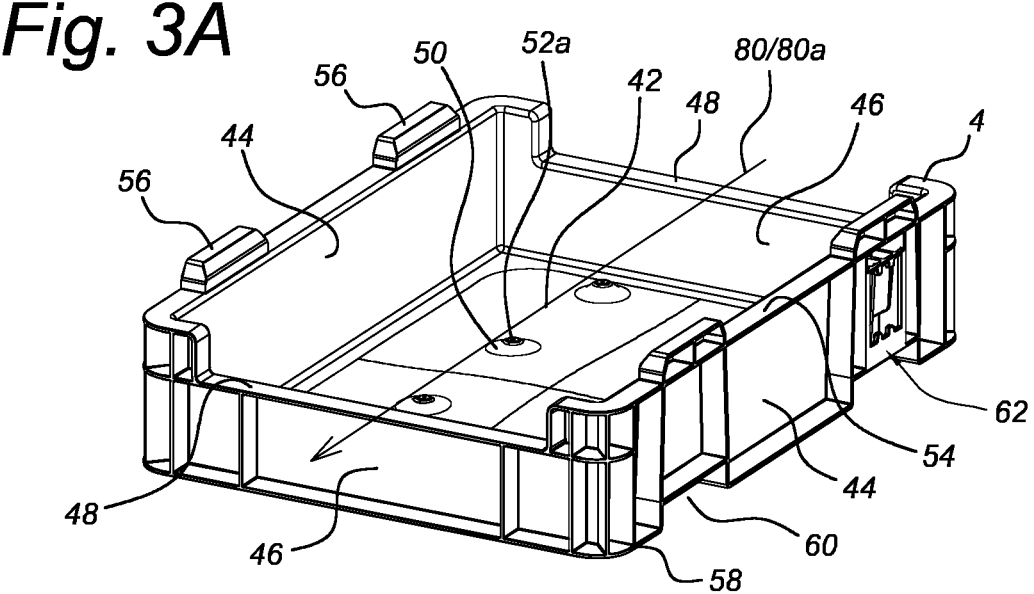
FIG. 3A shows a perspective view of an individual crate.

Moreover, as depicted in FIG. 3A and as described in more detail below, in a stack 6 comprising a plurality of crates 4 stacked on top of one another, the openings 48 in the side walls of the crates 4 create a plurality of air flow passage ways 80a extending through the stack 6 and preferably at equally spaced intervals.

In the embodiment shown in FIGS. 1A and B, a plurality of air inlets 18 and air outlets 20 are provided through a ceiling 22 of the chamber 2. The chamber 2 is optionally sub-divided into a plurality of sub-chambers 2a, 2b, each comprising e.g. two tracks 10, although such a chamber 2, 2a, 2b also may comprise a single track 10 or multiple tracks 10, more than two, such as three to ten tracks 10. The sub-division of the chambers 2a, 2b can be achieved by providing dividers 24, such as walls 24, separators 24, or curtains 24 and the like between tracks 10, e.g. between every single track 10 or two tracks 10 or three or more tracks 10. Preferably, the dividers 24 are spaced from the tracks 10 by a gutter 16. Accordingly, for example each chamber 2a, 2b comprises a first wall 26, a first gutter 28, a first track 30, a second gutter 32, a second track 34, a third gutter 36, and a second wall 24, e.g. the dividers 24, and a back wall 100 (front wall 100 not shown in FIG. 1A, front wall 100 shown in FIG. 5F).

Figure 5A:
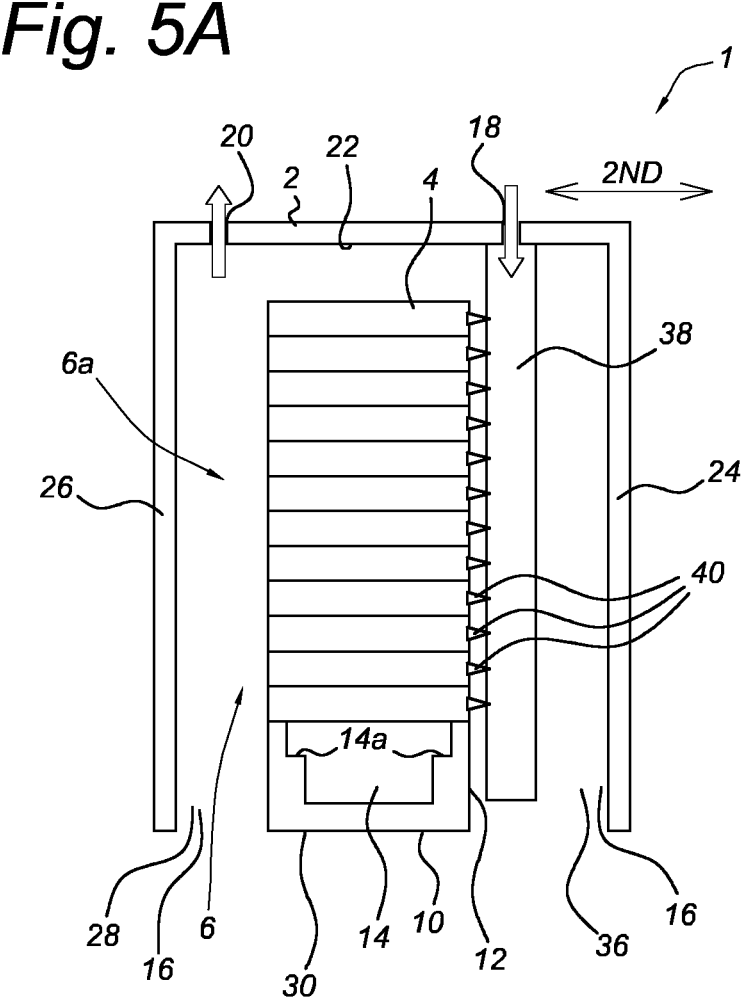
FIG. 5A shows a climate chamber in accordance with an embodiment of the invention, the climate chamber containing a plurality of crates.

As shown in FIG. 1A and FIG. 5C, the crates 4 are arranged such that the air inlets 18 are provided above the second gutter 32, between the first and second tracks 30, 34. In other words, the air inlets 18 open into the space between the first stack 6a of crates 4 and the second stack 6b of crates 4. The air outlets 20 are e.g. provided above the first and third gutters 28, 36 between the stack 6b of crates 4 and the dividers 24 and between the stack 6a of crates 4 and the first wall 26. Accordingly, the air outlets 20 open into the space between the track 34 and the second wall 24, and the track 30 and the first wall 26. Alternatively, in the embodiments of the system of the invention depicted in FIG. 5D and in FIG. 5E, positions of air inlets 18 and air outlets 20 are mutually exchanged compared to the embodiment of the system displayed in FIG. 1A-C. FIG. 5A displays a system 1 of the invention, which is the 'minimal' system of the invention, i.e. comprising a single (row of) air inlet(s) 18 and a single (row of) air outlet(s) 20. By arranging the air inlets 18 and air outlets 20 in this manner, climate controlled air can be introduced between the rows of stacked crates 4 and subsequently drawn through each stack 6 of crates 4 towards the air outlets 20, which are positioned on opposing sides of the stacks of crates 4. The air flow through the crates will be described in more detail with reference to FIG. 2.

As shown in FIGS. 1A and 2A and 5A and 5C, climate controlled air can be delivered from the air inlets 18 to the crates 4 via a conduit 38 extending from the air inlets 18 towards the gutter 16. The conduit 38 preferably comprises a series of openings 40, aligned with openings of the crates (described in more detail below). The conduit 38 may comprise a rigid conduit or a flexible conduit such as a hose or an air sock.

Figure 1C:
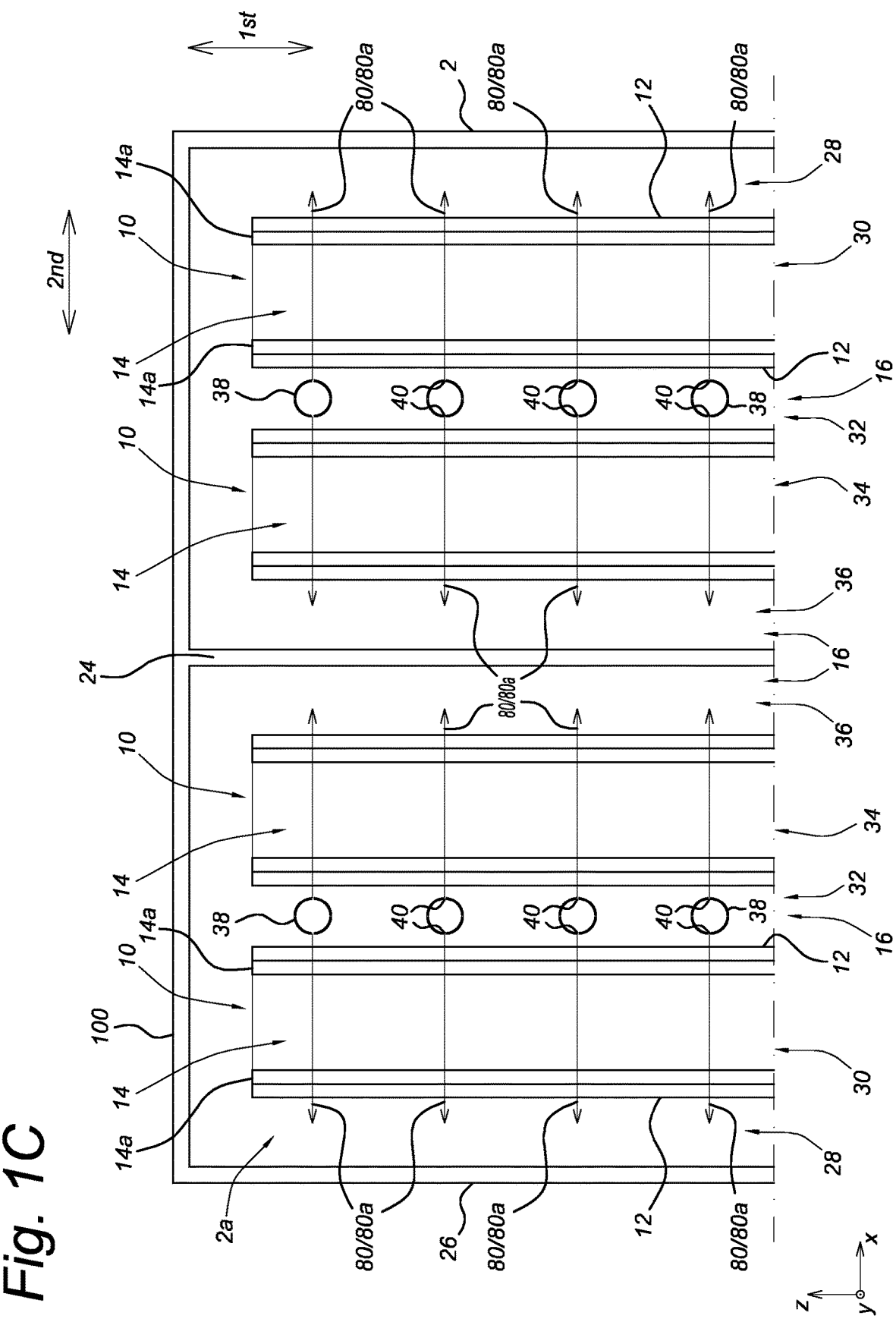
FIG. 1C shows a top view of the inner volume of the climate chamber shown in FIG. 1A in accordance with an embodiment of the invention, without crates 4 or pallets 8 positioned onto tracks 10.
Figure 4:
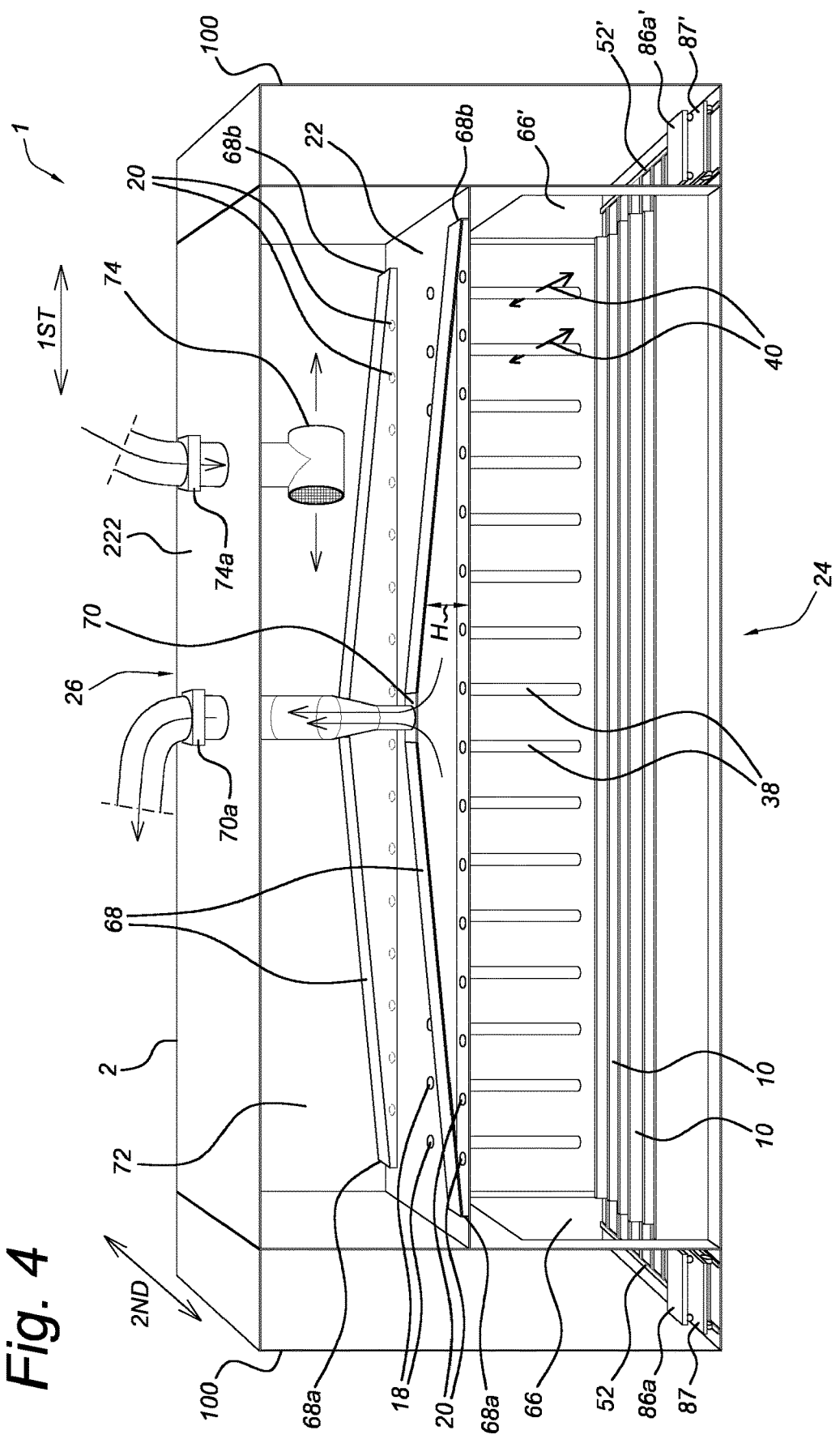
FIG. 4 shows a climate chamber according to an embodiment of the invention.
Figure 5B:
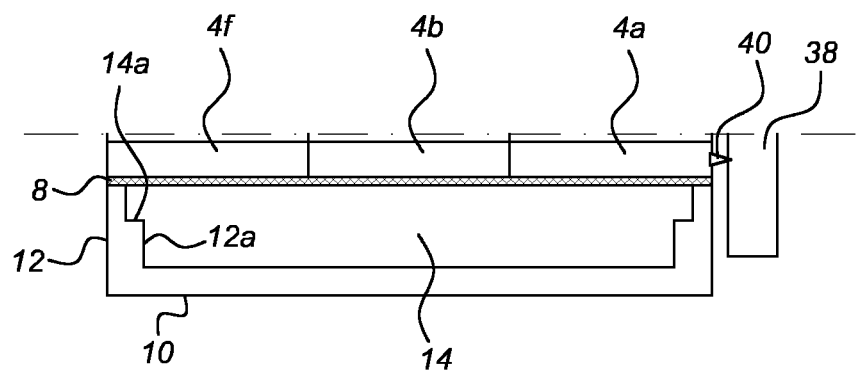
FIG. 5B shows a front view of a track with two walls defining a channel bearing a pallet and a plurality of stacks of crates.
Figure 5E:
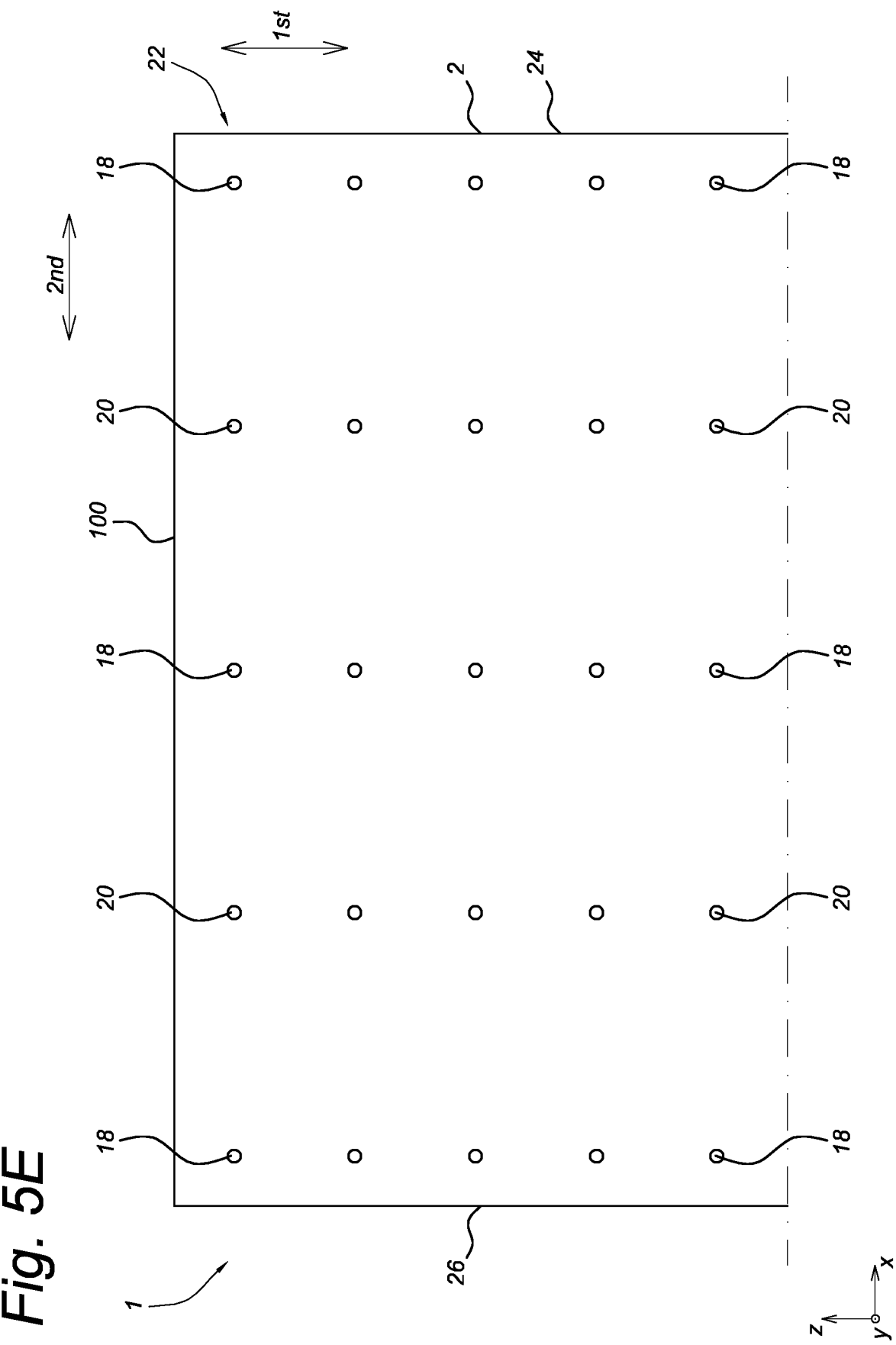
FIG. 5E shows a top view of a climate chamber in accordance with an embodiment of the invention, the climate chamber containing a plurality of air inlets 18 and air outlets 20.
Figure 5F:
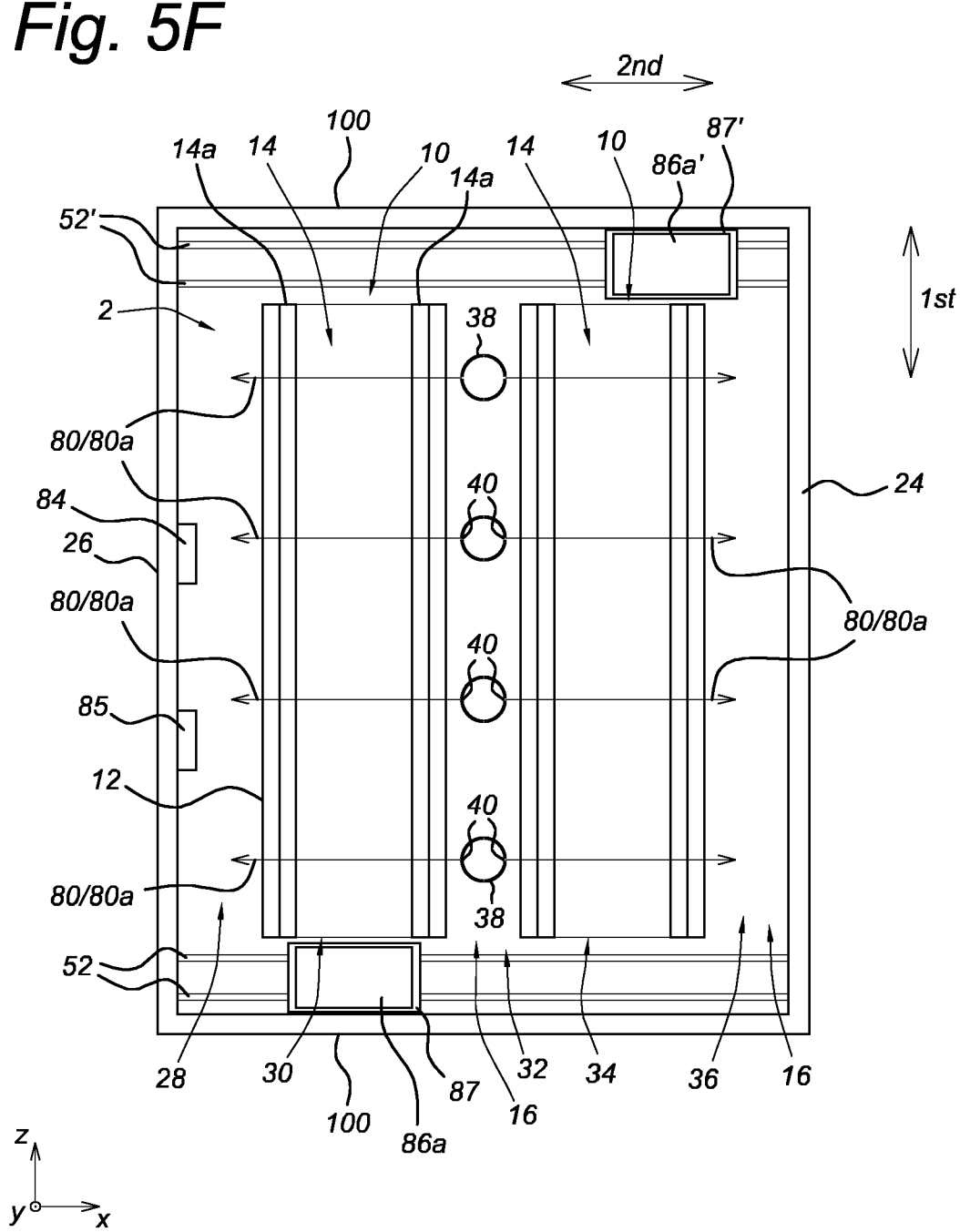
FIG. 5F shows a top view of the inner volume of a climate chamber in accordance with an embodiment of the invention, without crates 4 or pallets 8 positioned onto tracks 10.

In FIG. 1C, a top view of the inner volume of the climate chamber shown in FIGS. 1A and 1B, is shown, without pallets and crates placed onto walls 12 or ledges 14a. In FIG. 5F, a top view of the inner volume of the climate chamber shown in FIG. 4, is shown, without pallets and crates placed onto walls 12 or ledges 14a. Conduits 38 located between channels 14 are depicted, as well as flow paths 80a running perpendicular to the direction of the tracks 10. The skilled person will appreciate that the relative orientation of the combination of the tracks 10, bearing stacks 6 of crates, and the conduits 38 comprising the air openings 40 for delivering the flow paths 80a running perpendicular to the direction of the tracks 10, when the relative location of the side walls 24 and 26 and the front wall 100 and the back wall 100 is considered, can be freely established, as long as the air flow paths 80a run perpendicular to the direction of the tracks 10 such that air flows 80 can run over and through crates stacked onto walls 12 or ledges 14a, in the direction herein outlined. In the exemplary embodiment of the drawings, side walls run essentially parallel with the channels 14 and gutters 16, whereas the front wall and the back wall are oriented essentially perpendicular to the direction of the channels, which is preferred. Equally preferred is the orientation wherein the front and back walls run essentially parallel with the channels 14 and gutters 16, whereas the side walls are oriented essentially perpendicular to the direction of the channels.

An embodiment is the system 1 according to the invention, wherein the climate chamber 2 further comprises a plurality of air inlets 18 and a plurality of air outlets 20.

An embodiment is the system 1 according to the invention, wherein the at least one air inlet 18 and/or the at least one air outlet 20 are provided in a ceiling 22, 22a, 22b of the climate chamber 2.

An embodiment is the system 1 according to the invention, wherein the climate chamber 2 is divided into a plurality of sub-chambers 2a, 2b.

An embodiment is the system 1 according to the invention, wherein the climate chamber 2 is divided into a plurality of sub-chambers 2a, 2b, wherein each sub-chamber 2a, 2b has a first side wall 26 and a second side wall 24, and at least a first track 10 and a second track 10,
  wherein the first track is separated from the first wall by a first gutter 16, 28,
  wherein the first track is separated from the second track by a second gutter 16, 32, and
  wherein the second track is separated from the second wall by a third gutter 16, 36.

An embodiment is the system 1 according to the invention, wherein the plurality of air inlets 18 are arranged above the second gutter 16, 32, and wherein the plurality of air outlets 20 are arranged above the first gutter 16, 28 and the third gutter 16, 36, or wherein the plurality of air outlets 20 are arranged above the second gutter 16, 32, and wherein the plurality of air inlets 18 are arranged above the first gutter 16, 28 and the third gutter 16, 36.

An embodiment is the system 1 according to the invention, further comprising a control system 84 configured to maintain a pressure gradient between the inlet openings 18 and the outlet openings 20, wherein a pressure at the inlet openings is higher than a pressure at the outlet openings, such that air flows from the inlet openings, through the climate chamber 2, 2a, 2b, and out of the outlet openings.

Figure 2A:
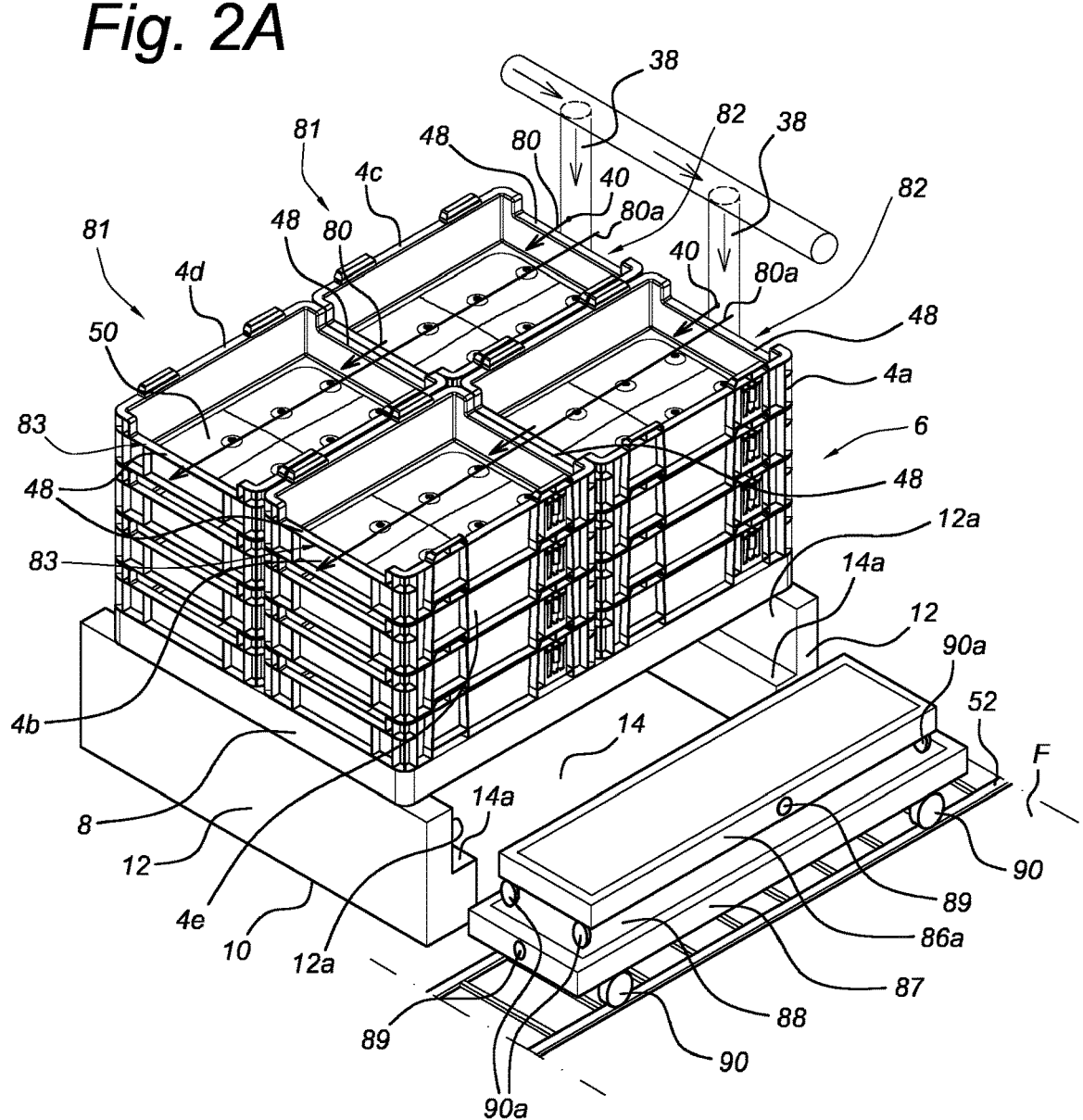
FIG. 2A shows a perspective view of a stack of crates from FIG. 1.
Figure 2B:
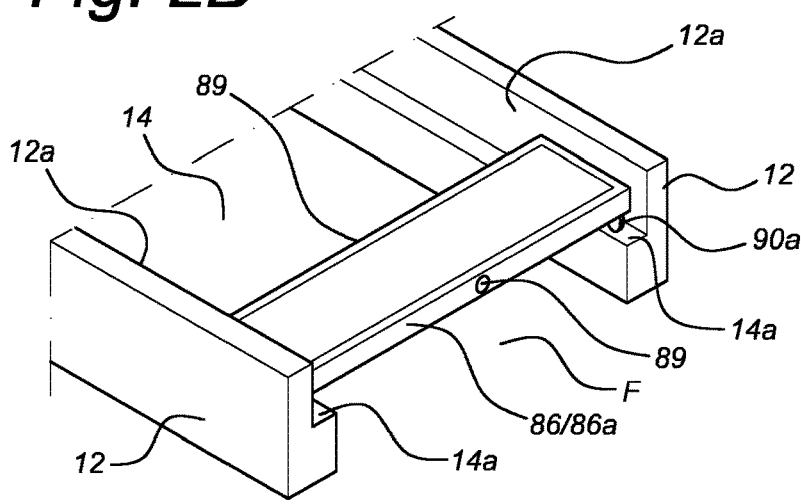
FIG. 2B shows a perspective view of a track with two walls defining a channel and a robotic device configured to move in the space defined by the walls.

A shown in FIG. 2A, to ensure a steady flow 80 of air through the crates 4, from an air inlet side 82 to an air outlet side 83 thereof, a pressure differential is preferably created between air inlet side 82 of the crates and the air outlet side 83, with a lower pressure at the outlet side 83. In an exemplary embodiment, the air inlet side 82 of the crates 4 is located proximal to the conduit 38. The pressure differential can be created by applying a pressure differential between air inlets 18 and the air outlets 20. As said, each track 10 can configured to support a pallet, the pallet comprising at least one stack of crates, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement. Alternatively, the pallet is absent, and multiple stacks 6 of horizontally stacked crates 4 are connected through crate connection means. When multiple crates are stacked in the second direction 2ND, i.e. the direction of the air flow paths 80a, the steady flow 80 of air runs through the multiple crates 4 stacked in the second direction 2ND, such as for example two crates 4 as depicted in FIG. 2A and three crates 4 as depicted in FIG. 5B, although crates 4 can also be provided as a single crate in stacks 6 when the second direction 2ND of flow path 80a is considered, or for example as horizontally stacked rows of more than four crates such as five to twelve crates. One or two crates stacked horizontally in the second direction 2ND is however preferred. Arrangements of 1, 2, 3, 4, 5, 6, 7 crates×any one of 1, 2, 3, 4, 5, 6, 7 crates are suitable according to the invention, although the invention is not limited to arrangements of 1, 1×2, 2×1, 2×2, . . . . 7×7 arrangements of a single crate or multiple crates, when stacks of crates are considered.

The climate chamber 2 shown in FIG. 1, FIG. 4 and FIG. 5 preferably further comprises a control system 84, configured to measure the conditions within each chamber 2 or each sub-chamber 2a, 2b and control the pressure differential between the air inlet(s) 18 and the air outlet(s) 20 accordingly. The chamber 2 and/or each sub-chamber 2a, 2b can also comprise sensors 85 configured to detect the temperature and humidity within the crates 4 and/or the chamber 2 or sub-chamber 2a, 2b and control the temperature and/or humidity of the air delivered through the air inlets 18 accordingly.

An embodiment is the system 1 according to the invention, further comprising at least one sensor 85 configured to measure at least one environmental condition within at least one of the plurality of crates. An embodiment is the system 1 according to the invention, wherein the at least one environmental condition includes one or more of:

temperature;
humidity;
oxygen concentration;
carbon dioxide concentration;
pressure; and
air flow.

An embodiment is the system 1 according to the invention, wherein the at least one sensor 85 is a sensor 52a arranged in a base 42 of the crates 4 (See FIG. 3). An embodiment is the system 1 of the invention, wherein the control system is configured to adjust at least one of the following parameters based on environmental conditions detected by at least one sensor:

temperature;
humidity;
oxygen concentration;
carbon dioxide concentration;
pressure at the inlet and/or outlet; and
air flow.

Further details of the system 1 will now be described with reference to FIG. 2, which shows a three dimensional view of a stack 6 of crates 4, e.g. in a 2×2 arrangement.

As shown in FIG. 2A, each pallet 8 supports four stacks 6 of crates 4, in a 2×2 arrangement. Each crate 4 comprises a base 42 and four upstanding walls: two opposing side walls 44, and two opposing end walls 46. The pellet 8 is optional. An arrangement of a single crate received by the upstanding walls 12 of the track 10, the crate bearing a stack of one or multiple crates, e.g. 1-20 crates, on top of this bottom crate, is equally suitable in the system of the invention.

One pair of opposing end walls 46 (see FIG. 3A) comprises openings 48 or cut-outs 48. The path 80a between the opposing openings 48 or cut-outs 48 defines an air flow path 80a over or through the crate 4.

The crates 4 are arranged with respect in the 2×2 arrangement in the same orientation such that two airflow paths 80a spanning two crates 4 are created. For example, a first 4a and a second 4b crate are arranged with their respective openings/cut-outs 48 aligned to define a first flow path 80a, whilst third 4c and fourth 4d crates are arranged with their respective openings 48 aligned to define a second flow path 80a. The first and second crates 4a, 4b are placed adjacent to the third and fourth crates 4c, 4d such that two parallel flow paths 80a are created.

The crates 4 in rows of stacked crates 81 are arranged such that the flow paths 80a extend perpendicular to the tracks 10. As shown in FIGS. 1A and 2A and 5B, this allows the crates 4 to be oriented with aligned openings 48 providing a flow path 80a between an inlet side 82 of the stack 6, 81, i.e. where the air inlets 18 are located, and an outlet side 83 of the stack 6, 81, i.e. where the air outlets 20 are located. Although the arrangement shown in FIG. 1 shows air inlet(s) 18 disposed between two tracks 10, and outlets 20 disposed on either side of the arrangement of two tracks 10, the skilled person will appreciate that the reverse arrangement is possible (with the air outlets 20 disposed above the second gutter 32 shown in FIG. 1 and the air inlets 18 disposed above the first gutter 28 and third gutter 36. See also FIGS. 5A, 5D and 5E in this regard.

However, the arrangement shown in FIGS. 1 and 5C is preferred in the illustrated example because the pressure differential from pressure to low pressure is inverse to the volume between the crates, e.g. the volume between the crates 4 shown in FIG. 1 is smaller than the volume on either side of the crates 4 and thus the pressure differential may be easier to control, and require less energy to maintain.

As shown in FIG. 2A, the crates 4 are configured to stack in a series of stacks 81 such that the openings 48 at opposing end walls 46 are aligned. In the embodiment illustrated in FIG. 3A, the crates 4 have an elongate cross-section, the opposing side walls 44 having a length L, and opposing end walls 46 having a length W, wherein W is less than L. The openings 48 are formed in the opposing end walls 46 of the crate 4, where the crates are arranged end to end in stacks 81 to form the flow path 80a mentioned earlier.

The opposing side walls 44 of the crate 4 not comprising the openings 48 are preferably configured such that they mate/cooperate with a crate above to provide a combined opposing side wall to the stack of crates 4 without openings. Such a configuration ensures that the flow of air through or over the crates 4 is restricted to the flow path 80a defined between the openings/cut-outs 48.

To further restrict air flow solely through the crates 4, the upstanding walls 12 of the track 10 on which the pallets 8 and/or crates 4 rest preferably comprise solid walls 12. Although an air tight seal between the pallets 8 and the upstanding wall 12 is not required, by providing solid walls, substantially free of openings, the volume of a flow path beneath the crates 4 between the air inlet side and the air outlet side that does not contribute to climate control within the crates 4 can be reduced or even eliminated.

As shown in FIG. 2A, the upstanding walls 12 on which the stacks 6 of crates 4 rest result in a channel 14 that extends under the crates 4. The channel 14 under the crates 4 may advantageously allow access to the volume beneath the crates 4 for various reasons. For example, an automated or remote controlled robotic device 86, 86a, 86a' (FIG. 2A, 2B, FIG. 4, FIG. 5F) can travel through the channel 14 beneath the crates 4. The robotic device 86, 86a, 86a' can be configured to monitor conditions along the length of the channel 14 (e.g. the robotic device is provided with sensors 89). Alternatively or additively, the robotic device 86, 86a, 86a' can be configured to retrieve stacks 6 of crates 4. It will be appreciated that the channel 14 also allows a manned lifting device to be manoeuvred along the channels 14.

The tracks 14 can further comprise a ledge 14a on an internal surface 12a of the upstanding wall 12, i.e. internal with respect to the channel 14, which provides runners along which the robot device 86 or manned lifting device can run. Such runners can allow a robotic device 86, 86a, 86a' to run along the channel 14 above the floor F of the chamber 2, or they can confine a robot 86, 86a, 86a' to a predetermined path.

The solid upstanding walls 12 that form the tracks 10 can provide a further advantage that they prevent escaped larvae or insects from entering the channel 14 under the crate stacks 6. Since the crates 4 are oriented with the airflow path 80a perpendicular to the channels 14, insects and/or larvae escaping from the crates 4 through the openings 48 fall into the gutters 16, and not into the channels 14 between the upstanding walls 12. Since the gutters 16 are separated from the channels 14 by solid walls 12, escaped insects and/or larvae are confined to the gutters 16, from which they can easily be cleaned.

The upstanding walls 12 may, in some embodiments, form a water tight seal between the channel 14 and the gutters 16. This can allow the gutters 16 to be washed without washing liquid running between the gutter 16 and the channels 14 under the upstanding walls 12 of the tracks 14. This can further help to keep the channels 14 beneath the crates 4 free of detritus, larvae, larvae remains, debris, cleaning liquid, etc., and to avoid contact between the robot 86, 86a or the manned lifting device, which runs in the channels 14 beneath the stacks 6 of crates 4, and the detritus, larvae, debris, larvae remains, cleaning liquid, etc. Avoiding the robot (and/or the manned lifting device) from contacting such waste products extends the operation time of the robot, prevents the robot from becoming damaged and prevents hampered performance of the robot. In addition, with a clean robot not contacted with said waste, the risk for contamination of the robotically lifted and transported crates 4 with said waste is avoided.

It will be appreciated that the channels 14 and the gutters 16 can be open at their respective ends, or that they can be formed with closed ends. In many embodiments, open ended channels 14 and/or gutters 16 are preferred since they facilitate access from the floor F of the climate chamber 2, e.g. for sweeping/cleaning or for robot 86, 86a, 86a' and/or lifting device access.

In at least one exemplary embodiment, the climate chamber 2 may further comprise one or more rails 52 running perpendicular to the channels 14, and configured to allow a robotic device 86, 86a, 86a' to move between channels 14. An embodiment is the system of the invention, wherein the climate chamber 2, 2a, 2b further comprises a first rail 52 extending in the second direction 2ND adjacent a first open end 66 of the at least one track 10 or adjacent a second open end 66' of the at least one track 10. An embodiment is the system of the invention, wherein the climate chamber 2, 2a, 2b further comprises a first rail 52 extending in the second direction 2ND adjacent a first open end 66 of the at least one track 10 and comprises a second rail 52' extending in the second direction 2ND adjacent a second open end 66' of the at least one track 10. An embodiment is the system of the invention, wherein the at least one track 10 comprises a ledge 14a on an internal surface of the upstanding wall with respect to the channel 14, which provides runners 14a along which a robot device or robot unit 86a, 86a' or manned lifting device can run. For example, the climate chamber 2, 2a, 2b can further comprise a rail or pair of rails 52 extending perpendicular to the channels 14 having an open end 66. The rails 52 can be configured to convey a (second or alternative) robotic device 87 in a perpendicular direction, in front of the open end of the channels 14. The second or alternative robotic device 87, 87' can comprise a frame 88 or carrier 88 configured to travel along the rail(s) 52, 52', and a robot unit 86a, 86a' configured to travel along the runners in the channel 14 formed by the ledges 14a. In embodiments, the open end 66, or the open ends 66 and 66' are optionally closable open ends, i.e. the openings 66, 66' can optionally be closed with e.g. a (sliding) door, slats, etc., when e.g. stacks of crates are not moved and/or the robotic unit or robotic device is not operating at or along rail 52, 52' and/or the robotic unit or robotic device is not operating at or over a track 10.

In an advantageous embodiment it is conceivable that the system 1 of the present invention comprises a robotic device 86, 86a, 86a', 87, 87' which is configured to move freely and place one or more crates 4 into the stacks 6 of crates 4, or take one or more crates 4 from stacks 6 of crates 4. This robotic device 86, 86a, 87 may be seen as a freely moveably warehouse-like robot that moves a crate/crates around, e.g. horizontally and/or vertically, in the chamber 2 and along any desirable (programmable) route. In an exemplary embodiment, such a robotic device 86, 86a, 87 may move on steerable wheels 90, 90a for maximum degrees of freedom.

Therefore, an advantageous embodiment is the system of the invention, wherein the first rail 52 and the second rail 52', when present, is/are configured to convey a robotic device 86a, 86a' in a perpendicular direction, i.e. the first direction 1ST along the direction in which track(s) 10 extent(s), in front of the first and/or second open end(s) 66, 66' of the channels, wherein optionally the robotic device comprises a frame or carrier configured to travel along the rail(s), and comprises a robot unit 86a, 86a' configured to travel along the at least one track or along the runners in the channel formed by the ledges 14a. An embodiment is the system of the invention, wherein the climate chamber further comprises at least one robotic device configured to move along the at least one track. Preferred is the embodiment relating to the system of the invention, further comprising at least one robotic device configured to freely move and place one or more crates into the first and/or the second stack of crates, or take one or more crates from the first and/or the second stack of crates.

As shown in FIGS. 1 and 2 and 5, a plurality of conduits 38 may be configured to deliver climate controlled air from the air inlet 18 directly to the openings 48 in the crates 4, the 2×2 arrangements thereof. Each conduits 38 can comprise a sock comprising a flexible wall, e.g. a polymer wall, having a plurality of openings 40. A conduit 38 preferably extends from the air inlet 18 provided in the ceiling of the climate chamber 2 towards the floor/bottom of the gutter 16. The conduits 38 are arranged such that they are preferably provided adjacent each stack of openings 48 of the stack of crates 4. Advantageously, the openings 40 in the conduit 38 are preferably spaced to align with individual openings 48 of the crates 4. In this manner, climate controlled air can be supplied from the conduits 38 to the openings 48 of the crates 4.

As shown in FIGS. 1 and 5C, each stack 6 of crates 4 is preferably configured such that an upper edge of a top crate 4T is positioned adjacent to the ceiling 22, 22a, 22b of the climate chamber 2, 2a, 2b. The upper edge 4U of the top crate is preferably positioned within 50 mm of the ceiling 22 of the climate chamber 2, more preferably within 30 mm of the ceiling 22, and more preferably within 20 mm of the ceiling of the climate chamber 2. This can allow a dead volume within the climate chamber 2 to be reduced, thus further improving the climate control within the chamber 2. Moreover, by minimising the space between the ceiling 22 and the top of each stack of crates, the space through which air can flow past the crates (without passing through the crates) is minimised. This may improve the efficiency of the system since it can help to maintain the pressure and/or temperature difference on either side of the stacks of crates 4.

The crate 4 of the present invention will now be described in more detail with reference to FIG. 3A-3B. FIG. 3A shows a perspective view of a single crate 4 according to an exemplary embodiment of the invention. As shown in FIG. 3A, the crate 4 comprises a base 42 providing a closed bottom to the crate 4. Upstanding walls 44, 46 extend from edges of the base 42 to provide the opposing side walls 44 and end walls 46 of the crate 4. The top of the crate 4 is open, although the skilled person will appreciate that the top of the crate 4 can also be provided with a lid 4L for closing/covering the top. In an exemplary embodiment, the crate 4 has a generally rectangular cross-section.

The openings 48 are formed in the opposing end walls 46, wherein the openings 48 may be formed as through holes, i.e. surrounded on all sides by the material of the end wall 46. Alternatively, and as shown in FIG. 3A, the openings 48 may be formed as recesses or cut-outs in an upper edge of the end walls 46 extending towards the base 42 of the crate 4.

The openings 48 preferably extend across at least 50% of the width of the end wall 46, more preferably at least 80% of the width of the end wall 46. Further, the openings 48 preferably comprise between 25 mm and 100 mm of the height of the crate 4, more preferably between 50 mm and 100 mm.

The base 42 of the crate is preferably smooth or substantially smooth, without ridges or recesses. By smooth it is meant that the base does not comprise planar surfaces that meet at a vertex having an angle of less than 130 degrees, more preferably 150 degrees, and more preferably 160 or 170 degrees. Preferably angled vertices are eliminated in the base 42 (except where the base 42 joins the walls 44, 46); and, in an embodiment in which the base 42 does not extend in a single plane, any transition between surfaces extending in different planes is curved, e.g. rounded corners. Such an arrangement may facilitate cleaning and hygiene of the crates.

The base 42 may further comprise one or more mounting points 50 for sensors 52a configured to measure various conditions, such as temperature, humidity, oxygen concentration, dry matter content etc. within the crates 4. In the example shown in FIGS. 2 and 3A, eight sensor mounting points 50 for each crate 4 are shown, however the skilled person will appreciate that fewer than eight sensor mounting points 50 can be provided.

Embodiments with more than eight sensor mounts 50 are also possible. The mounting points 50 for sensors 52a can comprise openings in the lower surface of the base 42 into which sensors 52a can be placed. In an advantageous embodiment, the sensors 52a may be configured to measure the conditions in the crate 4e below and/or in the crate 4b in which they are mounted.

In at least one embodiment, the sensor mounts 50 comprise a cavity extending into the interior volume of the crate 4 from the base 42. By providing a cavity that extends into the interior volume of the crate 4 in which a sensor 52a can be mounted, the sensor 52a can more accurately measure the conditions within the biomass contained in the crate. Multiple sensors 52a can be arranged within the base 42 of the crate 4, preferably equally spaced and arranged across the base 42 such that conditions throughout the biomass distributed in the crate 4 can be measured.

The openings in base 42 can be in direct communication with the interior volume of the crates 4, or a cover layer can be disposed between the sensors and the interior volume of the crates 4. The sensor(s) 52a can be in wired or wireless communication with control system 84 and/or with sensors 85 described above with reference to FIG. 1. Conditions detected by the sensors 52a can be used to adjust the flow rate of the air through the crates 4, the temperatures, and/or humidity of the air supplied through the air inlets 18, etc. Crates 4 according to the invention can be configured with integrated sensors or removable sensors 52a.

Alternatively, the control system 84 can be configured to operate according to set values, independent of the input of the sensors 52a and/or sensors 85. Instead, the sensors 52a can be used to monitor conditions within the climate chamber 2 without providing a direct feedback loop to the control unit.

Figure 3B:
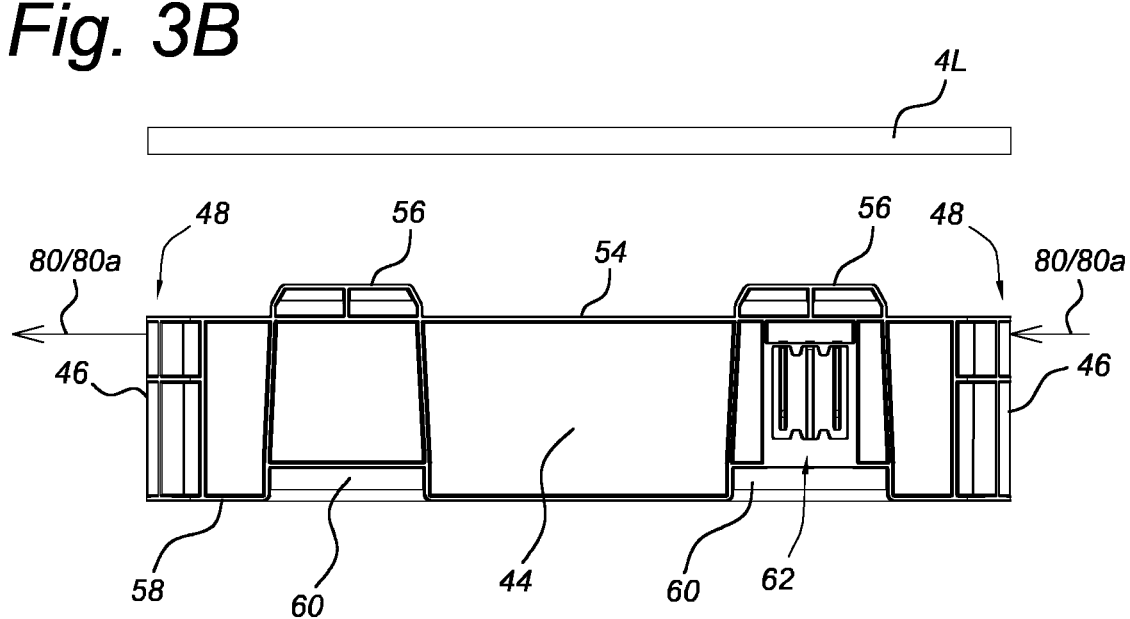
FIG. 3B shows a side view of the crate from FIG. 3A.

As further depicted in FIGS. 3A and 3B, each crate 4 may comprise a generally planar or flat upper edge 54. Each of the opposing side walls 44 may further comprise at least one (and preferably two) upstanding projections 56 extending from the upper edge 54 of the side walls 44.

A lower edge 58 of the side walls 44 preferably comprise a recess 60 configured to receive an upstanding projection 56 formed on an upper edge 54 of the crate 4e below when the crates 4 are stacked in alignment. This arrangement ensures alignment of the crates 4, and thus alignment of the crate openings 48 with each other, and with the openings 40 in the conduits 38.

Referring to FIG. 3B, a crate 4 may further comprise a receiving portion 62 for an identification tag, for example a radio frequency identification (RFID) tag. The RFID tag can be removably mounted in the receiving portion 62. The receiving portion 62 can take any form capable of receiving and retaining an identification tag. The tag can be slid, push fit, or magnetically retained in the receiving portion 62.

The projections 56 are preferably arranged on the opposing side walls 44 of the crate 4 such that the crate 4 has at least two-fold rotational symmetry about a vertical axis (with reference to projections 56). In other words, at least two projections 56 can be located on the crate 4 such that crates stack together as long as the side walls 44 are aligned with each other.

Similarly, the receiving portions 62 are preferably arranged on the side walls 44 of the crate 4 such that the crate has at least two fold-rotational symmetry about a vertical axis (with respect to receiving portions 62). In other words, at least two receiving portions 62 are provided, one on each side wall 44, i.e. lower edge 58, the receiving portions 60 being positioned such that they are in the relative position on the crate 4 as long as the side walls 44 are aligned. In the example shown in FIG. 3B, a receiving portions 62 is provided on the right hand side of the side wall 44, from the perspective of an observer facing the side wall 44 as depicted. On the opposing side wall 44, the receiving portion 62 is also provided on the right hand side of the side wall 44, from the perspective of an observer facing the opposing side wall 44. This can ensure that an identification tag is always visible in a stack of crates 4, and in a consistent location in a stack of crates 4.

The crate 4 can comprise a dual layer construction, having a structural exterior layer, which provides rigidity and structural stability, and an interior skin or layer, configured to provide a smooth interior surface. The smooth interior surface may also reduce the risk of larvae and/or insects escaping from the crate 4 or becoming lodged in crevices and recesses within the crate 4.

The dimensions of the crate 4 can be chosen according to the requirements of the climate chamber 2, the configuration of the tracks 10, and the developmental stage of the larvae and/or insects to be reared. For example, crates 4 configured for the rearing of neonate black soldier fly larvae, typically 0-5 days of age or 0-4 days of age can have: 400 mm length, 300 mm width, and 100 mm height. The skilled person will appreciate that other dimensions are also possible. For example, crates configured for the rearing of black soldier fly larvae, typically 3-25 days of age or 5-16 days of age can have: 800 mm length, 550 mm width, and 180 mm height.

Referring now to FIG. 4, and exemplary embodiment of a climate chamber 2 without crates 4 is shown.

As shown in FIG. 4, the chamber 2 comprises a single elongated chamber, comprising two parallel sets of tracks 10. Each track 10 extends from optionally a closed end 64 or an open end 66', to an open end 66; here in the embodiment of FIG. 4 from an open end 66 to and open end 66'. A first rail 52 may be arranged adjacent the open ends 66. A second rail 52' may be arranged adjacent the open ends 66'. The rails 52 and/or 52' may be configured to carry an electronic device between tracks 10, such as a robotic device 87, 87', optionally comprising a robotic unit 86a, 86a' for movement along the tracks 10 underneath the stacks 6 of crates.

The air inlets 18 and air outlets 20 are provided in the secondary ceiling 22 of chamber 2. As shown in FIG. 4, the air inlets 18 are supplied with climate controlled air via a master inlet 74 that is optionally provided with a driver 74a such as a pump or compressor for driving (conditioned) air into void 72 between ceiling 22 of the chamber 2 and the secondary ceiling of chamber 2, and subsequently driving the air into conduits 38 via air inlets 18. That is to say, the air inlets 18 are in communication with a void 72, which is in turn in communication with a master inlet 74. 20. An embodiment is the system according to the invention, wherein the system further comprises a second conduit and master air inlet 74 in fluid communication with the air inlets 18 and conduits 38 connected thereto, wherein the second conduit and master air inlet 74 is configured to push air into the climate chamber 2, that is to say, in the void 72 and through air inlets 18 into conduits 38.

An embodiment is the system according to the invention, wherein the plurality of air outlets 20 are arranged along a duct 68, wherein the duct is configured to draw air from the climate chamber 2 through the plurality of air outlets 20 via a master outlet 70. Optionally, the duct 68 has a variable height H, and the height of the duct 68 decreases as the distance from the master outlet 70 increases. The air outlets 20 are connected to a duct 68, e.g. covered or enclosed by the duct 68, along which the plurality of air outlets 20 are arranged. The ducts 68 are exhausted by a master outlet 70 in fluid communication with the duct 68. An embodiment is the system 1 according to the invention, wherein the duct 68 has a variable height H, and wherein the height of the duct 68 decreases as the distance from the master outlet 70 increases.

The duct 68 has a length P and extends along the length of the tracks 10. One duct 68 is provided per track 10. The master outlet 70 may be provided approximately half way along the length of the duct 68. The duct 68 has a height H that is greatest at the junction with the master outlet 70, and height H decreases as the duct 68 extends away from the master outlet 70 towards its opposing ends 68a, 68b. Such a tapering height of the duct 68 reduces the volume of the duct 68 as the duct 68 extends away from the master outlet 70. This reduction in volume can reduce the pressure drop along the length of the duct 68, thereby improving the consistency with which airflow is exhausted from the chamber 2 across the plurality of air outlets 20 arranged along the length of the duct 68.

It will be appreciated that a similar system can be employed with multiple ducts 68 provided along the length of the track 10. Each duct 68 may be provided with its own master outlet 70, and can comprise a maximum height H at the junction with the master outlet 70, with the height H reducing as the duct 68 extends away from the outlet 70 towards closed ends. It will be appreciated that a similar volume reduction can be achieved by varying other dimensions of the duct 68 as it extends away from the master outlet 70. Such configurations also fall within the scope of the present invention. In embodiments, the number of air outlets and the number of air inlets comprised by a chamber 2 are the same, or for example, the chamber 2 comprises a row or rows of air outlets 20 wherein the ratio between air outlets and air inlets in the chamber is one air outlet 20 for each two air inlets 18, or vice versa (2 to 1). Preferred is a system 1 comprising chamber 2 having a ratio between air outlets 20 and air inlets 18 of 1(:)2, although an alternative ratio will also suffice.

The plurality of air outlets 20 is also shown in FIG. 4, wherein the air outlets 20 are arranged in the ceiling 22 of chamber 2 above each of the two tracks 10 (see also FIG. 1, 5F). The air lets 18 are in communication with a void 72, which is in turn in communication with a master inlet 74.

It will be appreciated that flow of air 80 through the crates 4 may be controlled in different manners. For example, the only controlled parameter may be the flow of air 80 through the crates 4. This can be controlled by generating a pressure difference between the air inlets 18 and the air outlets 20. Such a pressure differential can be applied by applying a positive pressure (e.g. above atmospheric pressure) to the air inlet(s) 18 and/or a negative pressure (e.g. below atmospheric pressure) to the air outlet(s) 20.

Alternatively, one of the inlets 18 or the outlets 20 may be in fluid communication with a region of atmospheric pressure, whilst the other of the inlets 18 or the outlets 20 are controlled (either above or below atmospheric pressure) to provide the required pressure differential.

The climate can be further controlled by controlling the temperature and/or humidity of the air entering the climate chamber 2, e.g. sub chambers 2a, 2b, through the air inlets 18. The air flow 80 through the crates 4 and/or the temperature and/or humidity can be maintained at constant levels, or they can be varied cyclically, independently, or individually. The precise parameters desired for each climate chamber 2 or sub-chamber 2a, 2b depend on the insect species, developmental stage of the insects, and current production rate requirements, and can be chosen by the skilled person accordingly. Typically, the insect species reared in the crates 4 stacked in the chamber 2, 2a, 2b is the BSF, and typically, the developmental stage of said BSF is the neonate larvae stage for example between 0 and 5 days post hatching or between 0 and 4 days post hatching, or is the larvae stage for example between 4 and 20 days post hatching.

The airflow 80 (and/or the temperature and/or humidity of delivered air) can be further controlled based on environmental conditions measured by the sensors 52a and/or sensors 85. The control unit or control system 84 can be configured to adjust the supplied air in real time, or at predetermined intervals based on conditions detected by the sensors 52a. The controller can be configured to maintain the conditions within all sub-chambers 2a, 2b within a predetermined range, according to a set level. Alternatively, the control unit or the control system 84 can be configured to control the air supply to the sub-chambers 2a, 2b without sensor information. Instead, the sensors 52a can be used to issue an alert if the conditions deviate from a predefined set level.

Conditions within the sub-chambers 2a, 2b can be controlled individually. This arrangement can improve the consistency with which the larvae and/or insects are reared through each developmental stage. In many cases, it is preferably for large numbers of insects and/or larvae to develop at the same rate. According, the conditions in each sub-chamber 2a, 2b can be measured independently, and the airflow and climate control adjusted accordingly to harmonise, as far as possible, the rate of development of larvae and/or insects in each sub-chamber 2a, 2b.

A chamber 2 may house multiple sub-chambers 2a, 2b, each optimised for a different developmental stage or different species and/or different pace of development. In such embodiments, the crates 4 used in each such chamber 2a, 2b may comprise a different colour, indexed to indicate the developmental stage and/or species of larvae and/or insects. The colour coding of crates 4 can allow automatic detection of species and/or development stage, e.g. by a robotic device 86, 86a, 87 comprising an optical sensor 89, which can provide feedback to the climate control system and/or stock management information.

Thus, in summary, a first aspect of the invention relates to a system for rearing invertebrates, the system comprising:
a plurality of crates arranged into at least one stack, each crate in the stack defining an airflow path there through from an inlet opening in a first wall to an outlet opening in a second wall opposite the first wall; a climate chamber comprising: an internal volume enclosed by walls, a floor, and a ceiling; a first row of air outlets extending in a first direction within the internal volume; a second row of air outlets extending parallel to the first row of air outlets within the internal volume; a row of air inlets located between the first and second rows of air outlets, and extending parallel thereto, and spaced apart from the first and second rows of air outlets in a second direction, perpendicular to the first direction; at least one first stack of crates arranged in a space between the first row of air outlets and the row of air inlets; at least one second stack of crates arranged in a space between the second row of air outlets and the row of air inlets; a conduit extending from each of the plurality of air inlets between the first and second stack of crates, said conduit comprising a plurality of conduit openings configured to align with inlet openings of the plurality of crates in each stack; wherein the crates are arranged with the airflow path oriented perpendicular to the first direction.

An embodiment is the system according to the invention, wherein the climate chamber further comprises at least one track extending in the first direction with the climate chamber, said track comprising a first wall and a second wall, and a channel defined there between.

An embodiment is the system according to the invention, wherein the track is positioned between the first row of air outlets and the row of air inlets, and wherein the system, preferably, comprises a second track positioned between the row of air inlets and the second row of air outlets.

An embodiment is the system according to the invention, wherein the at least one track comprises a pair of walls separated from each other by a channel, said channel extending in the second direction, which is perpendicular to the first direction; and optionally, wherein the at least one stack of crates is arranged on the tracks such that the airflow path extends in the first direction.

An embodiment is the system according to the invention, wherein each track is configured to support a row of crate stacks above the channel.

An embodiment is the system according to the invention, wherein each track is configured to support a pallet comprising four stacks of crates arranged in a 2×2 arrangement.

An embodiment is the system according to the invention, wherein the pair of walls comprise solid, opposing walls, arranged parallel to each other.

An embodiment is the system according to the invention, wherein each of the walls is a solid wall and separates the channel from an adjacent gutter.

An embodiment is the system according to the invention, wherein the climate chamber further comprises a plurality of air inlets and a plurality of air outlets.

An embodiment is the system according to the invention, wherein the at least one air inlet and/or the at least one air outlet are provided in a ceiling of the climate chamber.

An embodiment is the system according to the invention, wherein the climate chamber is divided into a plurality of sub-chambers.

An embodiment is the system according to the invention, wherein each sub-chamber has a first side wall and a second side wall, and a first track and a second track, wherein the first track is separated from the first wall by a first gutter, wherein the first track is separated from the second track by a second gutter, and wherein the second track is separated from the second wall by a third gutter.

An embodiment is the system according to the invention, wherein the plurality of air inlets are arranged above the second gutter, and wherein the plurality of air outlets are arranged above the first and third gutters.

An embodiment is the system according to the invention, further comprising a control system configured to maintain a pressure gradient between the inlet openings and the outlet openings, wherein a pressure at the inlet openings is higher than a pressure at the outlet openings, such that air flows from the inlet openings, through the climate chamber, and out of the outlet openings.

An embodiment is the system according to the invention, further comprising at least one sensor configured to measure at least one environmental condition within at least one of the plurality of crates.

An embodiment is the system according to the invention, wherein the at least one environmental condition includes one or more of: temperature; humidity; oxygen concentration; carbon dioxide concentration; pressure; and air flow.

An embodiment is the system according to the invention, wherein the at least one sensor is arranged in a base of the crates.

An embodiment is the system according to the invention, wherein the plurality of air outlets are arranged along a duct 68, wherein the duct is configured to withdraw (extract, pull) air from chamber 2, 2a, 2b through the plurality of air outlets 20 via a master outlet 70.

An embodiment is the system 1 according to the invention, wherein the duct 68 has a variable height H, and wherein the height of the duct 68 decreases as the distance from the master outlet 70 increases.

An embodiment is the system according to the invention, wherein the system further comprises an air inlet conduit 74 through a through-hole in the (outer) ceiling of chamber 2 and in fluid communication with the air inlet openings 18, and wherein the conduit 74 comprises a flexible conduit comprising a plurality of holes along opposing sides. Conditioned air from outside the chamber 2 can be pulled into the void volume above ceiling 22, 22a, 22b of chamber 2, 2a, 2b and can be provided through air inlet openings 18 and into conduits 38 (see also FIG. 4).

An embodiment is the system according to the invention, wherein the climate chamber is provided in a static structure.

An embodiment is the system according to the invention, wherein the climate chamber is provided in a portable container, e.g. a shipping container, a reefer, a truck trailer.

An embodiment is the system according to the invention, wherein the control system is configured to adjust at least one of the following parameters based on environmental conditions detected by at least one sensor: temperature; humidity; oxygen concentration; carbon dioxide concentration; pressure at the inlet and/or outlet; and air flow.

An embodiment is the system according to the invention, wherein the climate chamber further comprises at least one rail extending in the second direction adjacent open ends of the at least one track.

An embodiment is the system according to the invention, wherein the at least one track comprises a ledge on an internal surface of the upstanding wall with respect to the channel, which provides runners along which a robot device or manned lifting device can run.

An embodiment is the system according to the invention, wherein the at least one rail is configured to convey a robotic device in a perpendicular direction, in front of the open end of the channels, wherein optionally the robotic device comprises a frame or carrier configured to travel along the rail(s), and comprises a robot unit configured to travel along the at least one track or along the runners in the channel formed by the ledges.

An embodiment is the system according to the invention, wherein the climate chamber further comprises at least one robotic device configured to move along the at least one track. An embodiment is the system according to the invention, further comprising at least one robotic device configured to freely move and place one or more crates into the first and/or the second stack of crates, or take one or more crates from the first and/or the second stack of crates.

The present invention also provides a method of rearing invertebrates, the method including the steps of: providing a plurality of crates 4; filling at least a portion of each crate 4 with a substrate and a plurality of invertebrates in a first developmental stage, and arranging said crates in a climate chamber 2 as described above to form a plurality of parallel air flow paths 80a through the crates 4.

The method further comprises passing a flow of air 80, preferably having controlled temperature and humidity, through said air flow paths 80a formed by said crates 4, by providing a plurality of air inlets 18 on a first side of said stack 6 of crates 4, and an air outlet 20 on an opposing side of said stack 6 of crates 4.

Optionally, the method further comprises measuring, with at least one sensor 52a disposed within the stack of crates 4, an environmental condition within the stack 6. Advantageously, the airflow 80 through the stack 6 can be modified based on the conditions detected by the sensor(s) 52a. Additionally or alternatively, the environmental condition in the volume surrounding the stack 6 in climate room 2, 2a, 2b is measured with at least one sensor 85 disposed in the climate room, outside crates 4, according to the method of the invention. Additionally or alternatively, the environmental condition in the volume surrounding the stack 6 in climate room 2, 2a, 2b is measured with at least one sensor 89 disposed on the robot 86, 86a, 87, according to the method of the invention.

The method further comprises the step providing a channel 14 extending in a first direction 1ST below a plurality of crate stacks 6, and arranging said stacks 6 with said airflow path 80a perpendicular to the first direction 1ST. Further optional and advantageous steps of a method according to the invention will be apparent from the above description of the exemplary system.

Like the system 1 as described above, the method of the present invention may further comprise the step of operating a robotic device 86, 87 to freely move and place one or more crates 4 into stacks 6 of crates 4 or take one or more crates 4 from the stacks of crates 4. Such a robotic device 86, 87 is operated like a freely movable warehouse robot which is able to move and manipulate one or more crates 4 along any desirable (programmable) route within the climate chamber 2. In an embodiment, the robotic device 86, 86a, 87 may have steerable wheels 90, 90a for achieving maximum degrees of freedom. The robotic device 87 can comprise a frame 88 or carrier 88 configured to travel along the rail(s), and a robot unit 86a configured to travel along the runners in the channel 14 formed by the ledges 14a.

The climate chamber 2 of the invention and the system 1 of the invention comprising the climate chamber 2 are particularly suitable for application in the method of the invention.

The crate 4 of the invention is particularly suitable for application in the method of the invention.

The crate 4 of the invention is particularly suitable for use in the climate chamber of the invention and for use in the climate chamber of the invention.

Thus, in summary, a second aspect of the invention relates to a method for rearing invertebrates, the method comprising the steps of: (i) providing a plurality of crates, each crate having a first opening in a first wall and a second opening in a second wall opposite the first opening to define a first air flow path between the first and second openings; (ii) filling at least a portion of each crate of the plurality of crates with a substrate and a plurality of invertebrates at a first developmental stage; (iii) stacking the plurality of crates; (iii) providing a climate chamber comprising: an internal volume; a climate chamber comprising: an internal volume enclosed by walls, a floor, and a ceiling; a first row of air outlets extending in a first direction within the internal volume; a second row of air outlets extending parallel to the first row of air outlets within the internal volume; a row of air inlets located between the first and second rows of air outlets, and extending parallel thereto, and spaced apart from the first and second rows of air outlets in a second direction, perpendicular to the first direction; at least one first stack of crates arranged in a space between the first row of air outlets and the row of air inlets; at least one second stack of crates arranged in a space between the second row of air outlets and the row of air inlets; a conduit extending from each of the plurality of air inlets between the first and second stack of crates, said conduit comprising a plurality of conduit openings configured to align with inlet openings of the plurality of crates in each stack; (iv) positioning at least one stack of crates wherein the crates are arranged with the airflow path oriented perpendicular to the first direction and in the second direction; (v) applying a pressure differential between the air inlet and the air outlet.

Referring to FIG. 4, an embodiment is the method according to the invention, wherein in step (iii) the climate chamber 2 is provided by providing a system 1 according to the invention. An embodiment is the method of the invention, wherein air is pulled out of the climate chamber via a duct 68, and wherein the air outlets 20 are arranged along said duct 68, which duct is configured to draw (pull, extract) air from the climate chamber 2 through the plurality of air outlets 20 via a master outlet 70. Duct 68 is (optionally) in fluid connection with a driver 70a such as a pump 70a for pulling or extracting or drawing air out of the climate chamber through air outlet openings 20, the duct 68 and master air outlet 70. Pulling air out of the climate chamber with the duct aids in creating under pressure at the side of the crates opposing the side of the crates near the openings 40 of the conduits 38, such that maintenance of the flow of air 80 along air flow path 80a is supported. An embodiment is the method according to the invention, wherein air is pushed into the climate chamber 2 via a second conduit 74 which is in fluid communication with the air inlets 18 and conduits connected thereto, and wherein the second conduit is configured to push air into the climate chamber. Pushing air into the climate chamber via the second conduit 74 (i.e. master inlet 74) aids in creating overpressure at the side of the crates near the openings 40 of the conduits 38, such that mainte-nance of the flow of air 80 along air flow path 80a is supported. Master inlet 74 is for example in fluid connection with a pump 74a or driver 74a for pushing air into void 74 and through air inlet openings 18 into conduits 38 (See FIG. 4). In the embodiment of FIG. 4, the drivers 70a and 70b are positioned outside the void 72 comprised by the chamber 2. In alternative embodiments, driver 70a and/or driver 74a is located inside void 72, although the embodiment displayed in FIG. 4 is preferred.

An embodiment is the method of the invention, wherein the climate chamber further comprises at least one track extending in the first direction with the climate chamber, said track comprising a first wall and a second wall, and a channel defined there between.

An embodiment is the method of the invention, wherein the at least one track is positioned between the first row of air outlets and the row of air inlets, and wherein the climate chamber (system) preferably comprises a second track positioned between the row of air inlets and the second row of air outlets.

An embodiment is the method of the invention, wherein the at least one track comprises a pair of walls separated from each other by a channel, said channel extending in a second direction, which is perpendicular to the first direction; and optionally, wherein the at least one stack of crates is arranged on the tracks such that the airflow path extends in the first direction.

An embodiment is the method of the invention, wherein the pair of walls comprise solid, opposing walls, arranged parallel to each other.

An embodiment is the method of the invention, wherein each of the walls is a solid wall and separates the channel from an adjacent gutter.

An embodiment is the method of the invention, wherein the method further comprises providing a plurality of air inlets and a plurality of air outlets, and positioning at least one stack of crates between an air inlet and an air outlet aligned with each other in the first direction.

An embodiment is the method of the invention, wherein the method further comprises: sensing, using at least one sensor, an environmental condition within one or more of the plurality of crates, wherein the sensed environmental condition can comprise one or more of: temperature; humidity; oxygen concentration; carbon dioxide concentration; pressure; and air flow.

An embodiment is the method of the invention, further comprising controlling at least one of the following parameters based on the sensed environmental conditions within the crates: temperature; humidity; oxygen concentration; carbon dioxide concentration; pressure at the inlet and/or outlet; and air flow.

An embodiment is the method of the invention, wherein the method further comprises arranging a plurality of stacks of crates in rows along the tracks, wherein each stack abuts an adjacent stack in the second direction.

An embodiment is the method of the invention, wherein the stacks are arranged in a 2×2 arrangement.

An embodiment is the method of the invention, further comprising, operating a robotic device to move along at least one track, wherein the robotic device is configured to: move at least one stack of crates along the tracks; detect environmental conditions within the channel; read information from at least one crate stacked above the channel.

An embodiment is the method of the invention, further comprising, operating a robotic device to freely move and:

place one or more crates into the first and/or the second stack of crates, or take one or more crates from the first and/or the second stack of crates.

An embodiment is the method of the invention, wherein the method further comprises conveying a robotic device in the second direction, in front of the open end of the channels, wherein the climate chamber comprises at least one rail extending in the second direction adjacent open ends of the at least one track wherein the at least one rail is configured to convey the robotic device, optionally the robotic device comprises a frame or carrier configured to travel along the rail(s), and comprises a robot unit configured to travel along the at least one track or along the runners in the channel formed by the ledges.

An embodiment is the method of the invention, further comprising running a robot device or manned lifting device along runners provided by the at least one track comprising a ledge on an internal surface of the upstanding wall with respect to the channel.

In summary, a further aspect of the invention relates to an invertebrate rearing crate configured for use in the system of the invention or in the method of the invention, wherein the crate comprises a base, upstanding side walls and upstanding end walls defining a perimeter around the base, and at least one sensor mounting region arranged in the base of the crate.

An embodiment is the invertebrate rearing crate according to the invention, wherein the base further comprises a plurality of sensors arranged in the base of the crate.

An embodiment is the invertebrate rearing crate according to the invention, wherein the crate further comprises at least one projection in an upper edge surface thereof, and at least a corresponding recess in a lower edge region, the recess being configured to receive a projection of a further crate stacked thereupon.

An embodiment is the invertebrate rearing crate according to the invention, wherein the crate further comprises a first receiving portion configured to receive a removable identification tag, e.g. an RFID tag.

An embodiment is the invertebrate rearing crate according to the invention, wherein the crate further comprises a second receiving portion positioned on an opposing side of the crate in a corresponding position, such that the position of the second receiving portion maps the position of the first receiving portion when the crate is rotated 180 degrees about a vertical axis.

An embodiment is the invertebrate rearing crate according to the invention, wherein the second receiving portion comprises an identification tag, e.g. an RFID tag.

It will be understood that the disclosed embodiments described above are exemplary configurations of the invention, which can be embodied in various forms. Therefore, specific structural and functional details disclosed herein are not to be interpreted as limiting. Rather, the examples described herein are intended to illustrate exemplary ways in which the invention may be put into effect.

The skilled person will understand that modifications can be made without departing from the scope of invention, which is defined by the appended claims.

Moreover, terms and phrases used herein are not intended to be limiting, but rather, to provide an understandable description of the invention.

The terms 'a' and 'an', as used in the present disclosure, are intended to mean one, or more than one. The term 'plurality', as used herein, is defined as two, or more than two.

The terms comprising, including and/or having, as used herein, are intended to mean 'including but not limited to', and a system, device or method comprising certain features and/or steps may include additional features and/or steps. Any reference signs in the claims should not be construed as limiting the scope of the claims or the invention.

The embodiments of the invention described herein can operate in combination and cooperation, unless specified otherwise.

Numbered Embodiments of the Invention with Reference to FIG. 1-5

1. A system 1 for rearing invertebrates, the system comprising:
    a plurality of crates 4 arranged into at least one stack 6, each crate in the stack defining an airflow path 80*a* there through from an inlet opening 48 in a first wall 46 to an outlet opening 48 in a second wall 46 opposite the first wall;
    a climate chamber 2, 2*a*, 2*b* comprising:
        an internal volume enclosed by walls 24, 26, a floor, and a ceiling 22;
        a first row of air outlets 20 extending in a first direction 1ST within the internal volume; a first row of air inlets 18 located next to the first row of air outlets 20, and extending parallel thereto, and spaced apart from the first row of air outlets in a second direction 2ND, perpendicular to the first direction 1ST;
        at least one first stack 6 of crates 4 arranged in a space between the first row of air outlets and the first row of air inlets;
        a conduit 38 extending from each of the plurality of air inlets along the first stack of crates, said conduit comprising a plurality of conduit openings 40 configured to align with inlet openings 48 of the plurality of crates 4 in the stack 6;
    wherein the crates are arranged with the airflow path 80*a* oriented perpendicular to the first direction 1ST.

2. The system for rearing invertebrates according to embodiment 1, the system comprising:
    a plurality of crates arranged into at least one stack, each crate in the stack defining an airflow path there through from an inlet opening in a first wall to an outlet opening in a second wall opposite the first wall;
    a climate chamber comprising:
        an internal volume enclosed by walls, a floor, and a ceiling;
        a first row of air outlets extending in a first direction within the internal volume;
        a second row of air outlets extending parallel to the first row of air outlets within the internal volume;
        a row of air inlets located between the first and second rows of air outlets, and extending parallel thereto, and spaced apart from the first and second rows of air outlets in a second direction, perpendicular to the first direction;
        at least one first stack of crates arranged in a space between the first row of air outlets and the row of air inlets;
        at least one second stack of crates arranged in a space between the second row of air outlets and the row of air inlets;
        a conduit extending from each of the plurality of air inlets between the first and second stack of crates, said conduit comprising a plurality of conduit openings configured to align with inlet openings of the plurality of crates in each stack;

or an internal volume enclosed by walls, a floor, and a ceiling;

a first row of air inlets extending in a first direction within the internal volume;

a second row of air inlets extending parallel to the first row of air inlets within the internal volume;

a first row of air outlets located between the first and second rows of air inlets, and extending parallel thereto, and spaced apart from the first and second rows of air inlets in a second direction, perpendicular to the first direction;

at least one first stack of crates arranged in a space between the first row of air inlets and the first row of air outlets;

at least one second stack of crates arranged in a space between the second row of air inlets and the first row of air outlets;

a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack;

wherein the crates are arranged with the airflow path oriented perpendicular to the first direction.

3. The system according to embodiment 1 or 2, wherein the plurality of crates are arranged into one to eight stacks, preferably any one of one, two, three, four, five, six stacks, more preferably any one of one, two or three stacks, most preferably one stack or two stacks, wherein the two or more stacks, when present, extend in the second direction perpendicular to the first direction with the climate chamber in the direction of the airflow path oriented perpendicular to the first direction.

4. The system according to any one of the embodiments 1-3, wherein the climate chamber further comprises at least one track 10 extending in the first direction 1ST with the climate chamber 2, 2a, 2b, said track comprising a first wall 12 and a second wall 12, and a channel 14 defined there between.

5. The system 1 according to any one of the embodiments 1-3, wherein the climate chamber 2, 2a, 2b further comprises at least one track 10 extending in the first direction 1ST with the climate chamber, said track comprising a first wall 12 and a second wall 12, and a channel 14 defined there between, wherein the track is positioned between the first row of air outlets 20 and the first row of air inlets 18, and wherein the system 1 preferably, when dependent on embodiment 2 or 3, comprises a second track 10 positioned between the first row of air inlets 18 and the second row of air outlets 20 or comprises a second track 10 positioned between the first row of air outlets 20 and the second row of air inlets 18.

6. The system 1 according to embodiment 4 or embodiment 5, wherein the at least one track 10 comprises a pair of walls 12 separated from each other by a channel 14, said channel extending in the second direction 2ND, which is perpendicular to the first direction 1ST; and optionally, wherein the at least one stack 6, 6a, 6b of crates 4 is arranged on the tracks 10 such that the airflow path 80a extends in the first direction 1ST.

7. The system 1 according to any one of the embodiments 4-6, wherein each track 10 is configured to support a row of crate stacks above the channel 14, the row of stacks extending in the first direction with the climate chamber 2, 2a, 2b.

8. The system 1 according to any one of the embodiments 4-7, wherein each track 10 is configured to support a pallet 8, the pallet comprising at least one stack 6 of crates 4, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement.

9. The system 1 according to embodiment 6, or any one of the embodiments 7 and 8 when dependent on embodiment 6, wherein the pair of walls 12 comprise solid, opposing walls, arranged parallel to each other.

10. The system 1 according to embodiment 6 or 9, wherein each of the walls 12 is a solid wall and separates the channel 14 from an adjacent gutter 16, 28, 32, 36.

11. The system 1 according to any one of the preceding embodiments, wherein the climate chamber 2, 2a, 2b further comprises a plurality of air inlets 18 and a plurality of air outlets 20.

12. The system 1 according to any one of the preceding embodiments, wherein the at least one air inlet 18 and/or the at least one air outlet 20 are provided in a ceiling 22, 22a, 22b of the climate chamber 2, 2a,2b.

13. The system 1 according to any one of the preceding embodiments, wherein the climate chamber 2 is divided into a plurality of sub-chambers 2a, 2b.

14. The system 1 according to embodiment 13, wherein each sub-chamber 2a, 2b has a first side wall 26 and a second side wall 24, and at least a first track 10 and a second track 10, wherein the first track is separated from the first wall by a first gutter 16, 28, wherein the first track is separated from the second track 10 by a second gutter 16, 32, and wherein the second track is separated from the second wall by a third gutter, 16, 36.

15. The system 1 according to embodiment 14, when depending from embodiment 11, wherein the plurality of air inlets 18 are arranged above the second gutter 16, 32, and wherein the plurality of air outlets 20 are arranged above the first and third gutters 16, 28, 36, or wherein the plurality of air outlets 20 are arranged above the second gutter 16, 32, and wherein the plurality of air inlets 18 are arranged above the first and third gutters 16, 28, 36.

16. The system 1 according to any one of the preceding embodiments, further comprising a control system 84 configured to maintain a pressure gradient between the inlet openings 18 and the outlet openings 20, wherein a pressure at the inlet openings is higher than a pressure at the outlet openings, such that air flows from the inlet openings, through the climate chamber, and out of the outlet openings.

17. The system 1 according to any one of the preceding embodiments, further comprising at least one sensor 85 configured to measure at least one environmental condition within at least one of the plurality of crates 4.

18. The system 1 according to embodiment 17, wherein the at least one environmental condition includes one or more of:

temperature;
humidity;
oxygen concentration;
carbon dioxide concentration;
pressure; and
air flow.

19. The system 1 according to embodiment 17 or 18, wherein the at least one sensor 85, 52a is arranged in a base 42 of the crates 4.

20. The system 1 according to embodiment 11 or any preceding embodiment depending from embodiment 11, wherein the plurality of air outlets 20 are arranged along a duct 68, wherein the duct 68 is configured to draw air from the climate chamber 2, 2a, 2b through the plurality of air outlets 20 via a master outlet 70.

21. The system 1 according to embodiment 20, wherein the duct 68 has a variable height H, and wherein the height of the duct 68 decreases as the distance from the master outlet 70 increases.

22. The system 1 according to embodiment 20 or embodiment 21, wherein the system further comprises a conduit 74 in fluid communication with the air inlets 18, and wherein the conduit comprises a flexible conduit comprising a plurality of holes along opposing sides.

23. The system 1 according to any one of the preceding embodiments, wherein the climate chamber 2, 2a, 2b is provided in a static structure.

24. The system 1 according to any one of the preceding embodiments, wherein the climate chamber is provided in a portable container, e.g. a shipping container, a reefer, a truck trailer.

25. The system 1 according to embodiment 16 or any one of the preceding embodiments depending from embodiment 16, wherein the control system 84 is configured to adjust at least one of the following parameters based on environmental conditions detected by at least one sensor 52a, 85:
  temperature;
  humidity;
  oxygen concentration;
  carbon dioxide concentration;
  pressure at the inlet and/or outlet; and
  air flow.

26. The system 1 according to any one of the preceding embodiments, when depending from embodiment 4 or 5, wherein the climate chamber 2, 2a, 2b further comprises a first rail 52 extending in the second direction 2ND adjacent a first open end 66 of the at least one track 10 or adjacent a second open end 66' of the at least one track 10.

27. The system 1 according to any one of the preceding embodiments, when depending from embodiment 4 or 5, wherein the climate chamber 2, 2a, 2b further comprises a first rail 52 extending in the second direction 2ND adjacent a first open end 66 of the at least one track 10 and comprises a second rail 52' extending in the second direction 2ND adjacent a second open end 66' of the at least one track 10.

28. The system 1 according to embodiment 26 or 27, wherein the at least one track 10 comprises a ledge 14a on an internal surface 12a of the upstanding wall 12 with respect to the channel 14, which provides runners 14a along which a robot device 86a, 86a' or manned lifting device can run.

29. The system 1 according to any one of the embodiments 26 or 27 or 28 when dependent on embodiment 26 or 27, wherein the first rail 52 and the second rail 52', when present, is/are configured to convey a robotic device 87 in a perpendicular direction, in front of the first and/or second open end(s) 66, 66' of the channels 14, wherein optionally the robotic device comprises a frame 88 or carrier 88 configured to travel along the rail(s) 52, 52', and comprises a robot unit 86a, 86a' configured to travel along the at least one track 10 or along the runners 14a in the channel 10 formed by the ledges 14a.

30. The system 1 according to any one of the preceding embodiments, when depending from embodiment 4 or 5, wherein the climate chamber 2, 2a, 2b further comprises at least one robotic device 86a, 86a' configured to move along the at least one track 10.

31. The system 1 according to any one of the embodiments 1-30, further comprising at least one robotic device 86a, 86a' configured to freely move and place one or more crates 4 into the first and/or the second stack 6, 6a, 6b of crates, or take one or more crates from the first and/or the second stack of crates.

32. A method for rearing invertebrates, the method comprising the steps of:
  (i) providing a plurality of crates, each crate having a first opening in a first wall and a second opening in a second wall opposite the first opening to define a first air flow path between the first and second openings;
  (ii) filling at least a portion of each crate of the plurality of crates with a substrate and a plurality of invertebrates at a first developmental stage;
  (iii) stacking the plurality of crates;
  (iii) providing a climate chamber comprising:
    an internal volume enclosed by walls, a floor, and a ceiling;
    a first row of air outlets extending in a first direction within the internal volume;
    a first row of air inlets located next to the first row of air outlets, and extending parallel thereto, and spaced apart from the first row of air outlets in a second direction, perpendicular to the first direction;
    at least one first stack of crates arranged in a space between the first row of air outlets and the first row of air inlets;
    a conduit extending from each of the plurality of air inlets along the first stack of crates, said conduit comprising a plurality of conduit openings configured to align with inlet openings of the plurality of crates in the stack;
  (iv) positioning at least one stack of crates wherein the crates are arranged with the airflow path oriented perpendicular to the first direction and in the second direction;
  (v) applying a pressure differential between the air inlet and the air outlet.

33. The method according to embodiment 32, wherein in step (iii) the climate chamber comprises:
  an internal volume enclosed by walls, a floor, and a ceiling;
  a first row of air outlets extending in a first direction within the internal volume;
  a second row of air outlets extending parallel to the first row of air outlets within the internal volume;
  a row of air inlets located between the first and second rows of air outlets, and extending parallel thereto, and spaced apart from the first and second rows of air outlets in a second direction, perpendicular to the first direction;
  at least one first stack of crates arranged in a space between the first row of air outlets and the row of air inlets;
  at least one second stack of crates arranged in a space between the second row of air outlets and the row of air inlets;
  a conduit extending from each of the plurality of air inlets between the first and second stack of crates, said conduit comprising a plurality of conduit openings configured to align with inlet openings of the plurality of crates in each stack;

or wherein in step (iii) the climate chamber comprises:

an internal volume enclosed by walls, a floor, and a ceiling;

a first row of air inlets extending in a first direction within the internal volume;

a second row of air inlets extending parallel to the first row of air inlets within the internal volume;

a first row of air outlets located between the first and second rows of air inlets, and extending parallel thereto, and spaced apart from the first and second rows of air inlets in a second direction, perpendicular to the first direction;

at least one first stack of crates arranged in a space between the first row of air inlets and the first row of air outlets;

at least one second stack of crates arranged in a space between the second row of air inlets and the first row of air outlets;

a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack.

34. The method according to embodiment 32 or 33, wherein the plurality of crates are arranged into one to eight stacks, preferably any one of one, two, three, four, five, six stacks, more preferably any one of one, two or three stacks, most preferably one stack or two stacks, wherein the two or more stacks, when present, extend in the second direction perpendicular to the first direction with the climate chamber in the direction of the airflow path oriented perpendicular to the first direction.

35. The method according to any one of the embodiments 32-34, wherein the climate chamber further comprises at least one track extending in the first direction with the climate chamber, said track comprising a first wall and a second wall, and a channel defined there between.

36. The method according to any one of the embodiments 32-34, wherein the climate chamber further comprises at least one track extending in the first direction with the climate chamber, said track comprising a first wall and a second wall, and a channel defined there between, wherein the track is positioned between the first row of air outlets and the first row of air inlets, and wherein the climate chamber preferably, when dependent on embodiment 33 or 34, comprises a second track positioned between the first row of air inlets and the second row of air outlets or comprises a second track positioned between the first row of air outlets and the second row of air inlets.

37. The method according to embodiment 35 or embodiment 36, wherein the at least one track comprises a pair of walls separated from each other by a channel, said channel extending in a second direction, which is perpendicular to the first direction; and optionally, wherein the at least one stack of crates is arranged on the tracks such that the airflow path extends in the first direction.

38. The method according to any one of the embodiments 35-37, wherein each track is configured to support a row of crate stacks above the channel, the row of stacks extending in the first direction with the climate chamber.

39. The method according to any one of the embodiments 35-38, wherein each track is configured to support a pallet, the pallet comprising at least one stack of crates, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement.

40. The method according to embodiment 37 or any one of the embodiments 38 and 39 when dependent on embodiment, 37, wherein the pair of walls comprise solid, opposing walls, arranged parallel to each other.

41. The method according to embodiment 37 or 40, wherein each of the walls is a solid wall and separates the channel from an adjacent gutter.

42. The method according to any one of the embodiments 37-41, wherein the method further comprises providing a plurality of air inlets and a plurality of air outlets, and positioning at least one stack of crates between an air inlet and an air outlet aligned with each other in the first direction.

43. The method according to any one of the embodiments 32-42, wherein the method further comprises: sensing, using at least one sensor, an environmental condition within one or more of the plurality of crates, wherein the sensed environmental condition can comprise one or more of:

temperature;
humidity;
oxygen concentration;
carbon dioxide concentration;
pressure; and
air flow.

44. The method according to embodiment 43, further comprising controlling at least one of the following parameters based on the sensed environmental conditions within the crates:

temperature;
humidity;
oxygen concentration;
carbon dioxide concentration;
pressure at the inlet and/or outlet; and
air flow.

45. The method according to any one of the embodiments 32-44, when depending from embodiment 35, wherein the method further comprises arranging a plurality of stacks of crates in rows along the tracks, wherein optionally each stack abuts at least one adjacent stack in the second direction, such as one, two, three or four adjacent stack(s), preferably one or two adjacent stacks, more preferably one adjacent stack in the second direction.

46. The method according to any one of the embodiments 32-45, wherein the stacks are arranged in a 2×1 or 1×2 arrangement, a 1×3 or 3×1 arrangement, a 2×2 arrangement, a 2×3 or 3×2 arrangement, a 3×3 arrangement, or any one of a 1×4, 4×1, 2×4, 4×2, 3×4, 4×3, 4×4, 1×5, 5×1, 2×5, 5×2, 3×5, 5×3, 4×5, 5×4 and 5×5 arrangement.

47. The method according to any one of the embodiments 32-46, further comprising, operating a robotic device to move along at least one track, wherein the robotic device is configured to:

move at least one stack of crates along the tracks;
detect environmental conditions within the channel;
read information from at least one crate stacked above the channel.

48. The method according to any of embodiments 32-47, further comprising, operating a robotic device to freely move and:

place one or more crates into the stack or stacks of crates, or take one or more crates from the stack or stacks of crates.

49. The method according to any one of the embodiments 32-48, further comprising running a robot device or robot unit or manned lifting device along runners provided by the at least one track comprising a ledge on an internal surface of the upstanding wall with respect to the channel.

50. The method according to any one of the preceding embodiments, wherein the method further comprises conveying a robotic device in the second direction, in front of the open end of the channels, wherein the climate chamber comprises a first rail extending in the second direction adjacent a first open end of the at least one track or adjacent a second open end of the at least one track, or wherein the climate chamber further comprises a first rail extending in the second direction adjacent a first open end of the at least one track and comprises a second rail extending in the second direction adjacent a second open end of the at least one track, wherein the first rail and/or the second rail, when present, is/are configured to convey the robotic device, optionally the robotic device comprises a frame or carrier configured to travel along the rail(s), and comprises a robot unit configured to travel along the at least one track or along the runners in the channel formed by the ledges.

51. The method according to any one of the preceding embodiments 32-50, wherein in step (iii) the climate chamber 2 is provided by providing a system 1 according to any one of the embodiments 1-31.

52. The method according to any one of the preceding embodiments 32-51, wherein air is pulled out of the climate chamber via a duct 68, and wherein the air outlets 20 are arranged along said duct 68, which duct is configured to draw air from the climate chamber 2 through the plurality of air outlets 20 via a master outlet 70.

53. The method according to embodiment 52, wherein air is pushed into the climate chamber 2 via a second conduit 74 which is in fluid communication with the air inlets 18 and conduits connected thereto, and wherein the second conduit is configured to push air into the climate chamber.

The invention claimed is:

1. A system for rearing invertebrates, the system comprising:
   a plurality of crates arranged into at least one stack, each crate in the stack defining an airflow path there through from an inlet opening in a first wall to an outlet opening in a second wall opposite the first wall;
   a climate chamber comprising:
     an internal volume enclosed by walls, a floor, and a ceiling;
     a first row of a plurality of air outlets extending in a first direction within the internal volume;
     a first row of a plurality of air inlets located next to the first row of air outlets, and extending parallel thereto, and spaced apart from the first row of air outlets in a second direction, perpendicular to the first direction;
     at least one first stack of crates arranged in a space between the first row of air outlets and the first row of air inlets;
     a conduit extending from each of the plurality of air inlets along the first stack of crates, said conduit comprising a plurality of conduit openings configured to align with inlet openings of the plurality of crates in the stack;
   wherein the crates are arranged with the airflow path oriented perpendicular to the first direction, wherein the plurality of air outlets are arranged along a duct and covered by the duct, and wherein the duct is configured to draw air from the climate chamber through the plurality of air outlets via a master outlet in fluid communication with the duct.

2. The system for rearing invertebrates according to claim 1, the system comprising:
   a plurality of crates arranged into at least one stack, each crate in the stack defining an airflow path there through from an inlet opening in a first wall to an outlet opening in a second wall opposite the first wall;
   a climate chamber comprising:
     an internal volume enclosed by walls, a floor, and a ceiling;
     a first row of air outlets extending in a first direction within the internal volume;
     a second row of air outlets extending parallel to the first row of air outlets within the internal volume;
     a row of air inlets located between the first and second rows of air outlets, and extending parallel thereto, and spaced apart from the first and second rows of air outlets in a second direction, perpendicular to the first direction;
     at least one first stack of crates arranged in a space between the first row of air outlets and the row of air inlets;
     at least one second stack of crates arranged in a space between the second row of air outlets and the row of air inlets;
     a conduit extending from each of the plurality of air inlets between the first and second stack of crates, said conduit comprising a plurality of conduit openings configured to align with inlet openings of the plurality of crates in each stack;
   or
     an internal volume enclosed by walls, a floor, and a ceiling;
     a first row of air inlets extending in a first direction within the internal volume;
     a second row of air inlets extending parallel to the first row of air inlets within the internal volume;
     a first row of air outlets located between the first and second rows of air inlets, and extending parallel thereto, and spaced apart from the first and second rows of air inlets in a second direction, perpendicular to the first direction;
     at least one first stack of crates arranged in a space between the first row of air inlets and the first row of air outlets;
     at least one second stack of crates arranged in a space between the second row of air inlets and the first row of air outlets;
     a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack;
   wherein the crates are arranged with the airflow path oriented perpendicular to the first direction.

3. The system according to claim 1, wherein the plurality of crates are arranged into one to eight stacks, preferably any one of one, two, three, four, five, six stacks, more preferably any one of one, two or three stacks, most preferably one stack or two stacks, wherein the two or more stacks, when present, extend in the second direction perpendicular to the first direction with the climate chamber in the direction of the airflow path oriented perpendicular to the first direction.

4. The system according to claim 1, wherein the climate chamber further comprises at least one track extending in the first direction with the climate chamber, said track comprising a first wall and a second wall, and a channel defined there between, or wherein the climate chamber further comprises at least one track extending in the first direction with the climate chamber, said track comprising a first wall and a second wall, and a channel defined there between, wherein the track is positioned between the first row of air outlets and the first row of air inlets.

5. The system according to claim 4, wherein the at least one track comprises a pair of walls separated from each other by a channel, said channel extending in the second direction, which is perpendicular to the first direction; and
   optionally, wherein the at least one stack of crates is arranged on the tracks such that the airflow path extends in the first direction; and/or,
   optionally, wherein each track is configured to support a row of crate stacks above the channel, the row of stacks extending in the first direction with the climate chamber; and/or,
   optionally, wherein each track is configured to support a pallet, the pallet comprising at least one stack of crates, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement; and/or,
   optionally, wherein the pair of walls comprise solid, opposing walls, arranged parallel to each other; and/or,
   optionally, wherein each of the walls is a solid wall and separates the channel from an adjacent gutter; and/or
   optionally, wherein the climate chamber further comprises a first rail extending in the second direction adjacent a first open end of the at least one track or adjacent a second open end of the at least one track; and/or,
   optionally, wherein the climate chamber further comprises a first rail extending in the second direction adjacent a first open end of the at least one track and comprises a second rail extending in the second direction adjacent a second open end of the at least one track; and/or,
   optionally, wherein the climate chamber further comprises at least one robotic device configured to move along the at least one track.

6. The system according to claim 1, wherein the climate chamber is divided into a plurality of sub-chambers, wherein each sub-chamber has a first side wall and a second side wall, and at least a first track and a second track,
   wherein the first track is separated from the first wall by a first gutter,
   wherein the first track is separated from the second track by a second gutter, and
   wherein the second track is separated from the second wall by a third gutter.

7. The system according to claim 6, wherein the plurality of air inlets are arranged above the second gutter, and wherein the plurality of air outlets are arranged above the first and third gutters, or wherein the plurality of air outlets are arranged above the second gutter, and wherein the plurality of air inlets are arranged above the first and third gutters.

8. The system according to claim 1, further comprising a control system configured to maintain a pressure gradient between the inlet openings and the outlet openings, wherein a pressure at the inlet openings is higher than a pressure at the outlet openings, such that air flows from the inlet openings, through the climate chamber, and out of the outlet openings;
   ; and,
   optionally, further comprising at least one sensor configured to measure at least one environmental condition within at least one of the plurality of crates, and,
   optionally, wherein, if present, the at least one environmental condition includes one or more of:
   temperature;
   humidity:
   oxygen concentration;
   carbon dioxide concentration;
   pressure; and
   air flow, and,
   optionally, wherein, if present, the at least one sensor is arranged in a base of the crates, and optionally, wherein, if present, the control system is configured to adjust at least one of the following parameters based on environmental conditions detected by at least one sensor:
   temperature;
   humidity;
   oxygen concentration;
   carbon dioxide concentration;
   pressure at the inlet and/or outlet; and
   air flow.

9. The system according to claim 1, wherein the duct has a variable height H, and wherein the height of the duct decreases as the distance from the master outlet increases.

10. The system according to claim 1, wherein the system further comprises a second conduit and master air inlet in fluid communication with the air inlets and conduits connected thereto, wherein the second conduit and master air inlet is configured to push air into the climate chamber.

11. The system according to claim 1, further comprising at least one robotic device configured to freely move and place one or more crates into the first and/or the second stack of crates, or take one or more crates from the first and/or the second stack of crates.

12. A method for rearing invertebrates, the method comprising the steps of:
   (i) providing a plurality of crates, each crate having a first opening in a first wall and a second opening in a second wall opposite the first opening to define a first air flow path between the first and second openings;
   (ii) filling at least a portion of each crate of the plurality of crates with a substrate and a plurality of invertebrates at a first developmental stage;
   (iii) stacking the plurality of crates;
   (iii) providing a climate chamber comprising:
      an internal volume enclosed by walls, a floor, and a ceiling;
      a first row of air outlets extending in a first direction within the internal volume;
      a first row of air inlets located next to the first row of air outlets, and extending parallel thereto, and spaced apart from the first row of air outlets in a second direction, perpendicular to the first direction;
      at least one first stack of crates arranged in a space between the first row of air outlets and the first row of air inlets;

a conduit extending from each of the plurality of air inlets along the first stack of crates, said conduit comprising a plurality of conduit openings configured to align with inlet openings of the plurality of crates in the stack;

(iv) positioning at least one stack of crates wherein the crates are arranged with the airflow path oriented perpendicular to the first direction and in the second direction;

(v) applying a pressure differential between the air inlet and the air outlet;

wherein air is pulled out of the climate chamber via a duct, and wherein the plurality of air outlets are arranged along said duct and covered by the duct, which duct is configured to draw air from the climate chamber through the plurality of air outlets via a master outlet in fluid communication with the duct, and, optionally, wherein air is pushed into the climate chamber via a second conduit which is in fluid communication with the plurality of air inlets and conduits connected thereto, and wherein the second conduit is configured to push air into the climate chamber.

13. The method according to claim 12, wherein in step (iii) the climate chamber comprises:
an internal volume enclosed by walls, a floor, and a ceiling;
a first row of air outlets extending in a first direction within the internal volume;
a second row of air outlets extending parallel to the first row of air outlets within the internal volume;
a row of air inlets located between the first and second rows of air outlets, and extending parallel thereto, and spaced apart from the first and second rows of air outlets in a second direction, perpendicular to the first direction;
at least one first stack of crates arranged in a space between the first row of air outlets and the row of air inlets;
at least one second stack of crates arranged in a space between the second row of air outlets and the row of air inlets;
a conduit extending from each of the plurality of air inlets between the first and second stack of crates, said conduit comprising a plurality of conduit openings configured to align with inlet openings of the plurality of crates in each stack;
or wherein in step (iii) the climate chamber comprises:
an internal volume enclosed by walls, a floor, and a ceiling;
a first row of air inlets extending in a first direction within the internal volume;
a second row of air inlets extending parallel to the first row of air inlets within the internal volume;
a first row of air outlets located between the first and second rows of air inlets, and extending parallel thereto, and spaced apart from the first and second rows of air inlets in a second direction, perpendicular to the first direction;
at least one first stack of crates arranged in a space between the first row of air inlets and the first row of air outlets;
at least one second stack of crates arranged in a space between the second row of air inlets and the first row of air outlets;
a conduit extending from each of the plurality of air inlets of the first row of air inlets to next to the first stack of crates and a conduit extending from each of the plurality of air inlets of the second row of air inlets to next to the second stack of crates, said conduits comprising a plurality of conduit openings configured to align with inlet openings of the plurality of crates in each stack.

14. The method according to claim 12, wherein the plurality of crates are arranged into one to eight stacks, preferably any one of one, two, three, four, five, six stacks, more preferably any one of one, two or three stacks, most preferably one stack or two stacks, wherein the two or more stacks, when present, extend in the second direction perpendicular to the first direction with the climate chamber in the direction of the airflow path oriented perpendicular to the first direction.

15. The method according to claim 12, wherein the climate chamber further comprises at least one track extending in the first direction with the climate chamber, said track comprising a first wall and a second wall, and a channel defined there between,, and,
optionally, wherein the at least one track comprises a pair of walls separated from each other by a channel, said channel extending in a second direction, which is perpendicular to the first direction; and,
optionally, wherein the at least one stack of crates is arranged on the tracks such that the airflow path extends in the first direction.

16. The method according to claim 15, wherein each track is configured to support a row of crate stacks above the channel, the row of stacks extending in the first direction with the climate chamber.

17. The method according to claim 15, wherein each track is configured to support a pallet, the pallet comprising at least one stack of crates, preferably comprising two stacks of crates arranged in a 2×1 or 1×2 arrangement, three stacks of crates arranged in a 1×3 or 3×1 arrangement, four stacks of crates arranged in a 2×2 arrangement, six stacks of crates arranged in a 2×3 or 3×2 arrangement, or nine stacks of crates arranged in a 3×3 arrangement.

18. The method according to claim 15, wherein the pair of walls, if present, comprise solid, opposing walls, arranged parallel to each other.

19. The method according to claim 15, wherein each of the walls is a solid wall and separates the channel from an adjacent gutter.

20. The method according to any one of the claims 12, wherein the method further comprises: sensing, using at least one sensor, an environmental condition within one or more of the plurality of crates, wherein the sensed environmental condition can comprise one or more of:
temperature;
humidity;
oxygen concentration;
carbon dioxide concentration;
pressure; and
air flow; and, optionally, further comprising controlling at least one of the following parameters based on the sensed environmental conditions within the crates:
temperature;
humidity;
oxygen concentration;
carbon dioxide concentration;
pressure at the inlet and/or outlet; and
air flow.

* * * * *